US012239400B2

(12) United States Patent
Kottenstette et al.

(10) Patent No.: US 12,239,400 B2
(45) Date of Patent: Mar. 4, 2025

(54) REMOTE COMMUNICATIONS AND CONTROL SYSTEM FOR ROBOTIC INTERVENTIONAL PROCEDURES

(71) Applicant: Corindus, Inc., Waltham, MA (US)

(72) Inventors: Nicholas Kottenstette, Sterling, MA (US); Yao Li, Belmont, MA (US); Per Bergman, West Roxbury, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 1021 days.

(21) Appl. No.: 17/055,427

(22) PCT Filed: May 17, 2019

(86) PCT No.: PCT/US2019/032888
§ 371 (c)(1),
(2) Date: Nov. 13, 2020

(87) PCT Pub. No.: WO2019/222641
PCT Pub. Date: Nov. 21, 2019

(65) Prior Publication Data
US 2021/0220064 A1    Jul. 22, 2021

Related U.S. Application Data

(60) Provisional application No. 62/719,757, filed on Aug. 20, 2018, provisional application No. 62/673,307, filed on May 18, 2018.

(51) Int. Cl.
*A61B 34/35*    (2016.01)
*A61B 34/00*    (2016.01)
(Continued)

(52) U.S. Cl.
CPC .............. *A61B 34/35* (2016.02); *A61B 34/77* (2016.02); *A61B 90/36* (2016.02); *G05B 19/406* (2013.01);
(Continued)

(58) Field of Classification Search
CPC ......... A61B 34/35; A61B 34/77; A61B 90/36; A61B 2090/365; A61B 2090/373;
(Continued)

(56) References Cited

U.S. PATENT DOCUMENTS 4,458,085 A * 7/1984 Huffman .............. C07D 333/60
549/57
4,759,570 A * 7/1988 Dandy, III ........... A63C 11/001
280/809

(Continued)

FOREIGN PATENT DOCUMENTS

CA    2395516 A1    5/2001
JP    2003285287    10/2003
(Continued)

OTHER PUBLICATIONS

Kyoman, et al., "The mobile robot teleoperation to consider the stability over the time delay of wireless network." Science and Technology, 2003. Proceedings Korus 2003. The 7th Korea-Russia International Symposium on Jun. 28-Jul. 6, 2003, IEEE. vol. 2, Jun. 28, 2003, pp. 457-461.
(Continued)

*Primary Examiner* — Bhavesh V Amin

(57) ABSTRACT

A method for using a control center at a remote site to control operation of a robotic medical device system at a local site includes transmitting a control signal from the control center to the robotic medical device system, determining a delay in transmission of the control signal, comparing the delay to a threshold delay value and operating the (Continued)

robotic medical device system based on the comparison of the delay to the threshold delay value.

36 Claims, 16 Drawing Sheets

(51) Int. Cl.
*A61B 90/00* (2016.01)
*G05B 19/406* (2006.01)
*G06F 17/11* (2006.01)

(52) U.S. Cl.
CPC ........ *G06F 17/11* (2013.01); *A61B 2090/365* (2016.02); *G05B 2219/40123* (2013.01); *G05B 2219/40151* (2013.01)

(58) Field of Classification Search
CPC ............ A61B 2090/3764; A61B 34/25; A61B 2034/742; A61B 2034/301; A61B 2090/376; A61B 2090/3762; A61B 2090/3782; A61B 34/30; G05B 19/406; G05B 2219/40123; G05B 2219/40151; G06F 17/11; B25J 9/1689; G16H 20/40; G16H 30/40; G16H 50/20; G16H 40/67; G16H 40/63
See application file for complete search history.

(56) References Cited

U.S. PATENT DOCUMENTS

| | | | | |
|---|---|---|---|---|
| 4,946,072 A * | 8/1990 | Albert | ................... | A47K 5/1215 |
| | | | | 222/105 |
| 5,038,089 A * | 8/1991 | Szakaly | ............... | G05B 19/427 |
| | | | | 700/251 |
| 5,515,478 A * | 5/1996 | Wang | ................... | A61B 34/70 |
| | | | | 700/262 |
| 5,524,180 A * | 6/1996 | Wang | ................... | B60R 21/0132 |
| | | | | 600/117 |
| 5,553,198 A * | 9/1996 | Wang | ................... | A61B 34/70 |
| | | | | 901/1 |
| 5,657,429 A * | 8/1997 | Wang | ................... | A61B 34/70 |
| | | | | 901/41 |
| 5,740,802 A * | 4/1998 | Nafis | ................... | H04N 13/239 |
| | | | | 703/2 |
| 5,754,741 A * | 5/1998 | Wang | ................... | A61B 34/70 |
| | | | | 700/262 |
| 5,762,458 A * | 6/1998 | Wang | ................... | A61B 34/71 |
| | | | | 606/130 |
| 5,815,640 A | 9/1998 | Wang et al. | | |
| 5,855,583 A * | 1/1999 | Wang | ................... | A61B 34/35 |
| | | | | 606/139 |
| 5,911,036 A * | 6/1999 | Wright | ................... | A61B 90/36 |
| | | | | 345/157 |
| 5,921,938 A * | 7/1999 | Aoyama | ................ | G16H 10/65 |
| | | | | 600/509 |
| 6,084,631 A * | 7/2000 | Tonkin | ............... | H04N 21/4363 |
| | | | | 348/E7.086 |
| 6,102,850 A * | 8/2000 | Wang | ................... | A61B 34/30 |
| | | | | 600/102 |
| 6,436,107 B1 * | 8/2002 | Wang | ................... | A61B 34/30 |
| | | | | 606/139 |
| 6,490,490 B1 * | 12/2002 | Uchikubo | ................ | A61B 1/04 |
| | | | | 700/246 |
| 6,496,099 B2 * | 12/2002 | Wang | ................... | G16H 40/40 |
| | | | | 606/1 |
| 6,574,355 B2 * | 6/2003 | Green | ................... | A61B 34/70 |
| | | | | 348/E13.016 |
| 6,642,836 B1 * | 11/2003 | Wang | ................... | A61B 17/00 |
| | | | | 704/E15.045 |
| 6,646,541 B1 * | 11/2003 | Wang | ................... | G16H 20/40 |
| | | | | 606/1 |
| 6,726,675 B1 * | 4/2004 | Beyar | ............... | A61M 25/0105 |
| | | | | 600/137 |
| 6,728,599 B2 * | 4/2004 | Wang | ................... | A61B 34/70 |
| | | | | 600/595 |
| 6,768,425 B2 * | 7/2004 | Flaherty | ............. | A61B 5/14532 |
| | | | | 128/920 |
| 6,785,593 B2 | 8/2004 | Wang et al. | | |
| 6,799,088 B2 | 9/2004 | Wang et al. | | |
| 6,836,703 B2 | 12/2004 | Wang et al. | | |
| 6,852,107 B2 * | 2/2005 | Wang | ................... | A61B 34/70 |
| | | | | 600/407 |
| 6,871,117 B2 | 3/2005 | Wang et al. | | |
| 6,892,112 B2 | 5/2005 | Wang et al. | | |
| 6,925,357 B2 * | 8/2005 | Wang | ................... | G05D 1/0038 |
| | | | | 700/261 |
| 6,950,691 B2 * | 9/2005 | Uchikubo | ............... | A61B 1/313 |
| | | | | 600/427 |
| 6,955,671 B2 * | 10/2005 | Uchikubo | ............... | A61B 1/042 |
| | | | | 606/1 |
| 7,239,940 B2 | 7/2007 | Wang et al. | | |
| 7,257,158 B1 * | 8/2007 | Figueredo | ............... | H04N 19/70 |
| | | | | 600/437 |
| 7,272,430 B2 | 9/2007 | Uchikubo | | |
| 7,386,730 B2 * | 6/2008 | Uchikubo | ............ | A61B 1/0005 |
| | | | | 606/1 |
| 7,480,806 B2 * | 1/2009 | Grawrock | ............. | H04L 63/123 |
| | | | | 713/185 |
| 7,485,115 B2 * | 2/2009 | Nakamura | ......... | A61B 1/00183 |
| | | | | 348/211.3 |
| 7,633,852 B2 * | 12/2009 | Brummette | ............. | F41H 11/28 |
| | | | | 370/464 |
| 8,135,413 B2 * | 3/2012 | Dupray | ................... | H04W 4/02 |
| | | | | 455/456.1 |
| 8,185,623 B2 * | 5/2012 | Lewis | ................... | G16H 40/20 |
| | | | | 709/224 |
| 8,321,284 B2 * | 11/2012 | Clements | ............... | G16H 10/60 |
| | | | | 600/509 |
| 8,340,819 B2 * | 12/2012 | Mangaser | ............. | G16H 40/67 |
| | | | | 700/250 |
| 8,396,598 B2 * | 3/2013 | Sutherland | ............ | A61B 34/71 |
| | | | | 901/14 |
| 8,401,869 B2 * | 3/2013 | Renzi | ............... | H04N 21/25891 |
| | | | | 600/300 |
| 8,621,445 B2 * | 12/2013 | Bangfei | ................ | G06F 9/541 |
| | | | | 717/136 |
| 8,631,506 B2 | 1/2014 | Wise et al. | | |
| 8,661,487 B2 * | 2/2014 | Pham | ................... | H04N 21/6587 |
| | | | | 725/107 |
| 8,670,017 B2 * | 3/2014 | Stuart | ................... | H04N 23/66 |
| | | | | 600/300 |
| 8,671,950 B2 | 3/2014 | Weitzner et al. | | |
| 8,731,777 B2 * | 5/2014 | Castaneda | ............. | B62D 6/002 |
| | | | | 701/2 |
| 8,806,051 B2 * | 8/2014 | Wang | ................... | H04L 67/06 |
| | | | | 709/231 |
| 8,868,234 B2 * | 10/2014 | Sanders | ............... | H04L 47/2433 |
| | | | | 901/6 |
| 8,897,152 B1 * | 11/2014 | Caceres | ............ | H04W 52/0229 |
| | | | | 370/252 |
| 8,924,234 B2 | 12/2014 | Renzi et al. | | |
| 9,001,216 B2 * | 4/2015 | Sampathkumaran | ........................ | |
| | | | | H04N 21/4223 |
| | | | | 348/207.1 |
| 9,105,200 B2 * | 8/2015 | Chen | ................... | G09B 23/28 |
| 9,131,259 B2 * | 9/2015 | Kim | ................... | G06F 3/0346 |
| 9,132,551 B2 * | 9/2015 | Zhang | ................... | B25J 9/1689 |
| 9,137,727 B2 * | 9/2015 | Kulkarni | ................ | H04W 48/02 |
| 9,191,425 B2 * | 11/2015 | Momchilov | ........... | H04L 65/612 |
| 9,203,883 B2 | 12/2015 | Momchilov et al. | | |
| 9,436,522 B2 * | 9/2016 | Choi | ................... | G06F 9/54 |
| 9,623,562 B1 * | 4/2017 | Watts | ................... | B25J 13/006 |
| 9,782,104 B2 * | 10/2017 | MacEachern | ........ | A61B 5/0022 |
| 9,820,658 B2 * | 11/2017 | Tran | ................... | A61B 5/7225 |
| 9,876,840 B2 * | 1/2018 | Nandakumar | ... | H04N 21/64322 |
| 9,973,638 B2 | 5/2018 | Pring | | |
| 10,069,887 B2 | 9/2018 | Hodapp | | |
| 10,320,875 B2 | 6/2019 | Bradbury et al. | | |

(56) References Cited

U.S. PATENT DOCUMENTS

| | | | |
|---|---|---|---|
| 10,594,483 B2 | 3/2020 | Smart | |
| 10,672,098 B1 | 6/2020 | Chemparathy et al. | |
| 11,399,906 B2* | 8/2022 | Shelton, IV | A61B 17/320068 |
| 2002/0147384 A1* | 10/2002 | Uchikubo | A61B 1/0005 600/109 |
| 2003/0028286 A1* | 2/2003 | Glenn | B25J 9/1689 700/259 |
| 2003/0046562 A1* | 3/2003 | Uchikubo | A61B 1/0005 713/189 |
| 2003/0093187 A1* | 5/2003 | Walker | B64D 45/0059 701/1 |
| 2003/0135203 A1* | 7/2003 | Wang | A61B 34/30 606/1 |
| 2003/0163711 A1* | 8/2003 | Grawrock | G06F 21/57 713/189 |
| 2003/0213698 A1* | 11/2003 | Kawagoshi | C23C 28/00 205/201 |
| 2004/0007445 A1* | 1/2004 | Demarest | B25J 9/1697 198/803.4 |
| 2004/0019406 A1* | 1/2004 | Wang | B25J 9/0003 700/231 |
| 2004/0236470 A1* | 11/2004 | Dooley | G05D 1/0033 700/255 |
| 2005/0038416 A1* | 2/2005 | Wang | G16H 40/67 606/1 |
| 2005/0047329 A1* | 3/2005 | Almog | H04L 69/16 370/225 |
| 2005/0057496 A1* | 3/2005 | Uchikubo | A61B 1/313 345/156 |
| 2005/0102065 A1* | 5/2005 | McBride | G06N 20/00 700/264 |
| 2005/0154288 A1* | 7/2005 | Wang | A61B 5/7475 600/407 |
| 2006/0025054 A1* | 2/2006 | Mayes | B24B 53/12 451/36 |
| 2006/0184272 A1* | 8/2006 | Okazaki | B25J 9/1697 700/245 |
| 2006/0276201 A1* | 12/2006 | Dupray | H04W 4/029 455/456.1 |
| 2007/0050828 A1* | 3/2007 | Renzi | H04N 7/163 348/E7.071 |
| 2007/0063834 A1* | 3/2007 | Bozzone | H04L 67/125 340/539.1 |
| 2007/0152619 A1* | 7/2007 | Sugiyama | B25J 9/1612 700/245 |
| 2007/0239186 A1* | 10/2007 | Weitzner | A61B 34/71 606/170 |
| 2008/0004904 A1* | 1/2008 | Tran | G16H 40/67 340/286.07 |
| 2008/0015415 A1* | 1/2008 | Obata | G02B 23/2484 348/E5.042 |
| 2008/0082210 A1* | 4/2008 | Kim | B63B 35/32 700/255 |
| 2008/0089881 A1 | 4/2008 | Li et al. | |
| 2008/0133126 A1* | 6/2008 | Dupray | G01S 13/878 701/408 |
| 2008/0161784 A1* | 7/2008 | Hogan | A61B 5/055 600/410 |
| 2008/0179115 A1* | 7/2008 | Ohm | B62D 55/075 901/1 |
| 2009/0006858 A1* | 1/2009 | Duane | H04L 9/3234 713/185 |
| 2009/0036750 A1* | 2/2009 | Weinstein | G16H 40/67 600/300 |
| 2009/0132281 A1* | 5/2009 | Lyshkow | G06Q 10/109 705/3 |
| 2009/0222539 A1* | 9/2009 | Lewis | G16H 40/67 600/509 |
| 2009/0248043 A1* | 10/2009 | Tierney | A61B 46/13 606/130 |
| 2009/0314554 A1* | 12/2009 | Couture | B25J 5/005 180/9.1 |
| 2010/0063630 A1* | 3/2010 | Sutherland | A61B 34/71 700/264 |
| 2010/0070079 A1* | 3/2010 | Mangaser | G16H 40/63 700/259 |
| 2010/0129112 A1* | 5/2010 | Tada | G03G 5/0696 430/59.5 |
| 2010/0250000 A1* | 9/2010 | Blumenkranz | A61B 18/00 74/490.06 |
| 2010/0278086 A1* | 11/2010 | Pochiraju | H04W 28/20 370/310 |
| 2011/0010013 A1* | 1/2011 | Ruan | B25J 5/007 901/1 |
| 2011/0088070 A1* | 4/2011 | Pham | H04N 21/4227 725/109 |
| 2011/0138069 A1* | 6/2011 | Momchilov | H04L 65/765 709/231 |
| 2011/0145431 A1* | 6/2011 | Momchilov | H04L 65/765 709/231 |
| 2011/0198136 A1* | 8/2011 | Teague | B62D 51/04 180/19.1 |
| 2011/0218674 A1* | 9/2011 | Stuart | H04L 65/403 700/259 |
| 2011/0275907 A1* | 11/2011 | Inciardi | A61B 5/1112 600/301 |
| 2011/0306986 A1* | 12/2011 | Lee | A61B 34/37 606/130 |
| 2012/0139923 A1* | 6/2012 | Bangfei | G06F 9/541 345/473 |
| 2012/0185115 A1* | 7/2012 | Dean | G05D 1/0038 701/2 |
| 2012/0191464 A1* | 7/2012 | Stuart | G16H 30/20 901/1 |
| 2012/0227113 A1* | 9/2012 | Wise | G06F 21/53 709/217 |
| 2012/0317278 A1* | 12/2012 | Tamaki | H04L 1/0018 709/224 |
| 2013/0006417 A1* | 1/2013 | Sanders | H04L 47/13 375/295 |
| 2013/0085602 A1* | 4/2013 | Fung | B25J 11/003 700/245 |
| 2013/0085774 A1* | 4/2013 | Chen | G09B 23/28 703/11 |
| 2013/0117867 A1* | 5/2013 | Fung | G06F 21/88 726/35 |
| 2013/0123980 A1* | 5/2013 | Seo | G05D 1/0027 700/248 |
| 2013/0138736 A1* | 5/2013 | Wang | H04L 67/06 709/204 |
| 2013/0201273 A1* | 8/2013 | Renzi | H04N 21/47202 348/14.01 |
| 2013/0204430 A1* | 8/2013 | Davey | G06F 30/13 700/216 |
| 2013/0282173 A1* | 10/2013 | Gunday | A61B 34/72 901/30 |
| 2013/0290015 A1* | 10/2013 | Johnson | G16H 40/67 705/2 |
| 2013/0325244 A1* | 12/2013 | Wang | G16H 40/67 701/26 |
| 2013/0331650 A1* | 12/2013 | Blumenkranz | G02B 6/32 600/130 |
| 2014/0019993 A1* | 1/2014 | Mathur | G06F 9/5094 719/313 |
| 2014/0039277 A1* | 2/2014 | Abraham | A61B 8/0841 600/301 |
| 2014/0159849 A1* | 6/2014 | Bae | H01F 17/0013 29/605 |
| 2014/0222248 A1* | 8/2014 | Levien | G08G 5/0013 701/2 |
| 2014/0331261 A1* | 11/2014 | Kim | H04N 21/42206 725/52 |
| 2015/0197010 A1* | 7/2015 | Ruuspakka | G05D 1/0005 700/245 |
| 2015/0203213 A1* | 7/2015 | Levien | G08G 5/0013 701/486 |
| 2015/0231784 A1* | 8/2015 | Yamauchi | G05D 1/0088 901/1 |

(56) References Cited

U.S. PATENT DOCUMENTS

| | | | | |
|---|---|---|---|---|
| 2015/0280913 | A1* | 10/2015 | Smart | G06F 12/1408 |
| | | | | 713/193 |
| 2015/0298318 | A1* | 10/2015 | Wang | B25J 9/1689 |
| | | | | 700/257 |
| 2015/0347682 | A1* | 12/2015 | Chen | G16H 50/20 |
| | | | | 705/2 |
| 2016/0114888 | A1* | 4/2016 | Downey | B64U 10/14 |
| | | | | 701/2 |
| 2016/0140851 | A1* | 5/2016 | Levy | G08G 5/0069 |
| | | | | 701/410 |
| 2017/0043483 | A1* | 2/2017 | Fine | B25J 9/1676 |
| 2017/0050747 | A1* | 2/2017 | Wessler | B64D 47/06 |
| 2017/0106530 | A1* | 4/2017 | Shimokawa | G05B 19/042 |
| 2017/0182664 | A1* | 6/2017 | Watts | B25J 9/1689 |
| 2017/0189096 | A1* | 7/2017 | Danziger | A61B 18/1206 |
| 2017/0214807 | A1* | 7/2017 | Pring | H04L 69/04 |
| 2017/0215261 | A1* | 7/2017 | Potucek | G05D 21/02 |
| 2018/0003067 | A1* | 1/2018 | Bidkar | F01D 5/02 |
| 2018/0024247 | A1* | 1/2018 | Carter | G01S 19/06 |
| | | | | 342/357.26 |
| 2018/0069980 | A1* | 3/2018 | Miyata | H04N 1/2104 |
| 2018/0292827 | A1* | 10/2018 | Artes | G01C 21/362 |
| 2020/0405414 | A1* | 12/2020 | Shelton, IV | A61B 17/320092 |
| 2023/0017152 | A1* | 1/2023 | Morimura | H04J 3/0667 |

FOREIGN PATENT DOCUMENTS

| | | |
|---|---|---|
| JP | 2005261956 A | 9/2005 |
| JP | 2006107050 | 4/2006 |
| JP | 2007325960 | 12/2007 |
| JP | 2007325960 A | 12/2007 |
| JP | 2009044413 | 2/2009 |
| JP | 2009519017 | 5/2009 |
| JP | 2009519107 | 5/2009 |
| JP | 2011028495 A | 2/2011 |
| JP | 2015047666 | 3/2015 |
| JP | 2016515847 | 6/2016 |
| KR | 20100078034 | 7/2010 |
| KR | 1020100078034 A | 7/2010 |
| WO | 2004012018 | 2/2004 |
| WO | 2004012018 A2 | 2/2004 |
| WO | 2011109336 | 9/2011 |
| WO | 2011109336 A2 | 9/2011 |
| WO | 2012140294 A1 | 10/2012 |
| WO | 2013008252 A2 | 1/2013 |

OTHER PUBLICATIONS

Partial European Search Report for Corresponding European Application No. EP19804224, mailed Jun. 8, 2002.

Garcia, Pablo, et al. "Trauma Pod: a semi-automated telerobotic surgical system." The International Journal of Medical Robotics and Computer Assisted Surgery 5.2 (2009): 136-146.

Avgousti, Sotiris, et al. "Medical telerobotic systems: current status and future trends." Biomedical engineering online 15.1 (2016): 96.

Anvari et al.; Establishment of the World's First Telerobotic Remote Surgical Service; Annals of Surgery; Mar. 2005; pp. 460-464; vol. 241, No. 3; Lippincott Williams & Wilkins.

Avgousti et al.; Medical telerobotic systems: current status and future trends; BioMedical Engineering OnLine (2016) 15:96; Published online Aug. 12, 2016; 40 pages.

International Search Report and Written Opinion for PCT/US2019/032888; mail date Aug. 29, 2019; 12 pages.

Macrae; The Robo-Doctor Will See You Now; May 2012; https://www.asme.org/engineering-topics/articles/robotics/robo-doctor-will-see-you-now; retrieved on Jan. 19, 2014; 5 pages.

Parsell; Surgeons in U.S. Perform Operation in France Via Robot; nationalgeographic.com/news; Sep. 19, 2001; http://news.nationalgeographic.com/news/pf/15081787.html; retrieved on Jan. 19, 2014; 3 pages.

Saenz; Remote Controlled Robot Performs Heart Surgery on British Man; http://singularityhub.com/2010/0505/remote-controlled-robot-performs-heart-surgery-on-. . . ; posted May 5, 2010; retrieved Jan. 19, 2014; 5 pages.

SRI International; AM7 Surgical Robot; http://www.sri.com/engage/products-solutions/m7-surgical-robot; retrieved on Jan. 20, 2014; 1 page.

Yeongho Kim et al.; "Collaborative surgical simulation over the Internet"; IEEE Internet Computing; Jun. 30, 2001 (Jun. 30, 2001); pp. 65-73.

Frank Tobias et al: "ROS-IGTL-Bridge: an open network interface for image-guided therapy using the ROS environment", International Journal of Computer Assisted Radiology and Surgery, Springer, DE, vol. 12, No. 8, May 31, 2017 (May 31, 2017), pp. 1451-1460.

David A Wollman et al.; "Framework for cyber-physical systems: vol. 3; timing annex NIST SP 1500-203"; NIST; National Institute of Standards and Tecnology (NIST); vol. 1.0; Sep. 28, 2017 (Sep. 28, 2017); pp. 1-84.

"CAR Posters"; International Journal of Computer Assisted Radiology and Surgery; A Journal for Interdisciplinary Research; Development and Applications of Image Guided Diagnosis and Therapy; Springer Berlin; DE; vol. 1; No. 7; May 23, 2006 (May 23, 2006); pp. 461-485.

Hori Kenta; "Chapter 8: Information Support for Telesurgery" In: "Telesurgery"; Nov. 30, 2007 (Nov. 30, 2007); Springer Berlin Heidelberg, Berlin; Heidelberg; XP055954091; ISBN: 978-3-540-72998-3 pp. 101-111.

European Search Report for Corresponding Application No. 19804224.4.

* cited by examiner

REMOTE COMMUNICATIONS AND CONTROL SYSTEM FOR ROBOTIC INTERVENTIONAL PROCEDURES

CROSS-REFERENCE TO RELATED APPLICATION

This application is based on, claims priority to, and incorporates herein by reference in its entirety U.S. Ser. No. 62/719,757, filed Aug. 20, 2018, and entitled "Remote Communications System And Control System For Robotic Medical Devices" and U.S. Ser. No. 62/673,307, filed May 18, 2018, and entitled "Remote Communications System And Control System For Robotic Medical Devices."

FIELD

The present invention relates generally to the field of robotic medical procedure systems and, in particular, to a remote communications and control system for devices used in robotic interventional procedures.

BACKGROUND

Catheters (and other elongated medical devices) may be used for many minimally-invasive medical procedures for the diagnosis and treatment of diseases of various vascular systems, including neurovascular interventional (NVI) also known as neurointerventional surgery, percutaneous coronary intervention (PCI) and peripheral vascular intervention (PVI). These procedures typically involve navigating a guidewire through the vasculature, and via the guidewire advancing a working catheter to deliver therapy. The catheterization procedure starts by gaining access into the appropriate vessel, such as an artery or vein, with a sheath or guide catheter using standard percutaneous techniques. The sheath or guide catheter is then advanced over a diagnostic guidewire to the primary location such as an internal carotid artery for NVI, a coronary ostium for PCI or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example a lesion. Contrast-enhanced images are also obtained while the physician delivers the guidewire or catheter device so that the physician can verify that the device is moving along the correct path to the target location. While observing the anatomy using fluoroscopy, the physician manipulates the proximal end of the guidewire or catheter to direct the distal tip into the appropriate vessels toward the lesion and avoid advancing into side branches.

Robotic catheter procedure systems have been developed that may be used to aid a physician in performing catheterization procedures such as, for example, NVI, PCI and PVI. Examples of neurovascular intervention (NVI) catheter procedures include coil embolization of aneurysms, liquid embolization of arteriovenous malformations and mechanical thrombectomy of large vessel occlusions in the setting of acute ischemic stroke. In NVI, the physician uses a robotic system to gain lesion access by manipulating a neurovascular guidewire and microcatheter to deliver the therapy to restore normal blood flow. The access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several coils are deployed into the aneurysm through the microcatheter and used to embolize the aneurysm. For treating arteriovenous malformations, a liquid embolic is injected into the malformation via a microcatheter. Mechanical thrombectomy to treat vessel occlusions can be achieved either through aspiration or use of a stent retriever. Aspiration is either done directly through the microcatheter, or with a larger bore aspiration catheter. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or FFR measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

Typically, an operator of the robotic system used for the medical procedure is located in the same room or an adjacent room to the patient and robotic system. It may be desirable, however, to allow an operator located at a remote location (e.g., a different building, a different city) to operate the robotic system to perform the medical procedure. A system that allows an operator at a remote location to control and operate a robotic medical procedure system provides patients in, for example, smaller communities access to medical specialists that may not be available locally. In addition, patients requiring emergency medical procedures may be treated at a local hospital by a specialist located remotely which can decrease the time before an interventional procedure is performed. For example, it is advantageous to complete an interventional procedure to treat a patient with an acute ischemic stroke due to large vessel occlusion (LVO), or to treat a patient with ST-segment-elevation myocardial infarction (STEMI) as soon as possible. Various remote surgical systems have been developed for general, vascular, cardiac and urological procedures. For example, remote surgical systems have been used for laparoscopic procedures. There are many challenges in developing a system for an operator to perform a medical procedure remotely. A secure network connection over a network (e.g., the Internet) must be established and maintained. Delays and jitter in transmission of control signals and images can affect the safety of the procedure as well as the stability of the system. Deadlock with regard to control of the local medical procedure system can occur between the local and the remote location. There can also be challenges to providing a many-to-many configuration that allows multiple remote locations to connect with and operate the local medical procedure system.

SUMMARY

In accordance with an embodiment, a method for using a control center at a remote site to control operation of a robotic medical device system at a local site includes transmitting a control signal from the control center to the robotic medical device system, determining a delay in transmission of the control signal, comparing the delay to a threshold delay value and operating the robotic medical device system based on the comparison of the delay to the threshold delay value.

In accordance with another embodiment, a method for using a control center at a remote site to control operation of an elongated medical device in a robotic medical device system at a local site including receiving a control signal from the control center, determining a delay in transmission of the control signal, determining a threshold delay value based on at least one parameter of the robotic medical device system, comparing the delay to the threshold delay value and adjusting the operation of the elongated medical device based on the comparison of the delay to the threshold delay value.

In accordance with another embodiment, a method for using a control center at a remote site to control operation of a robotic medical device system at a local site includes receiving a control signal from the control center, determining a delay in transmission of the control signal, comparing the delay to a threshold delay value and if the delay is less than the threshold delay value, adjusting a velocity of a medical device of the robotic medical device system based on the delay and if the delay is greater than the threshold delay value, setting the velocity of the medical device to zero.

In accordance with another embodiment, a system for controlling a medical device includes a control center located at a remote site. The control center includes a control console, a first command and control module coupled to the control console and a first clock coupled to the first command and control module using a precision time protocol, the first clock configured to receive time data from a reference time source. The system further includes a robotic medical device system at a local site, the robotic medical device system in communication with the control center. The robotic medical secives system includes at least one medical device, a second command and control module coupled to the at least one medical device and in communication with the first command and control module and a second clock coupled to the second command and control module using the precision time protocol, the first clock configured to receive time data from the reference time source. The control center and the remote medical device system communicate over a secure tunnel. The control console of the control center is configured to communicate with and control the at least one medical device.

In accordance with another embodiment, a system for managing control of at least one medical device by a remote site and a local site includes a control center located at a remote site, a robotic medical device system at a local site, the robotic medical device system in communication with the control center and a virtual control token for determining a control state for the control center and the robotic medical device system. The location of the virtual control token determines the control state.

In accordance with another embodiment, a method for reducing bandwidth for transmission of data from a robotic medical device system at a local site to a control center at a remote site where the control center configured to control the operation of the robotic medical device system includes generating a display of the data at the robotic medical device system, The data includes at least one image and non-image patient information. The method further includes selecting a section of the generated display, transmitting the selected section of the display to the control center and displaying the selected section on a display of the control center.

BRIEF DESCRIPTION OF THE DRAWINGS

The invention will become more fully understood from the following detailed description, taken in conjunction with the accompanying drawings, wherein the reference numerals refer to like parts in which.

DETAILED DESCRIPTION

Figure 1:
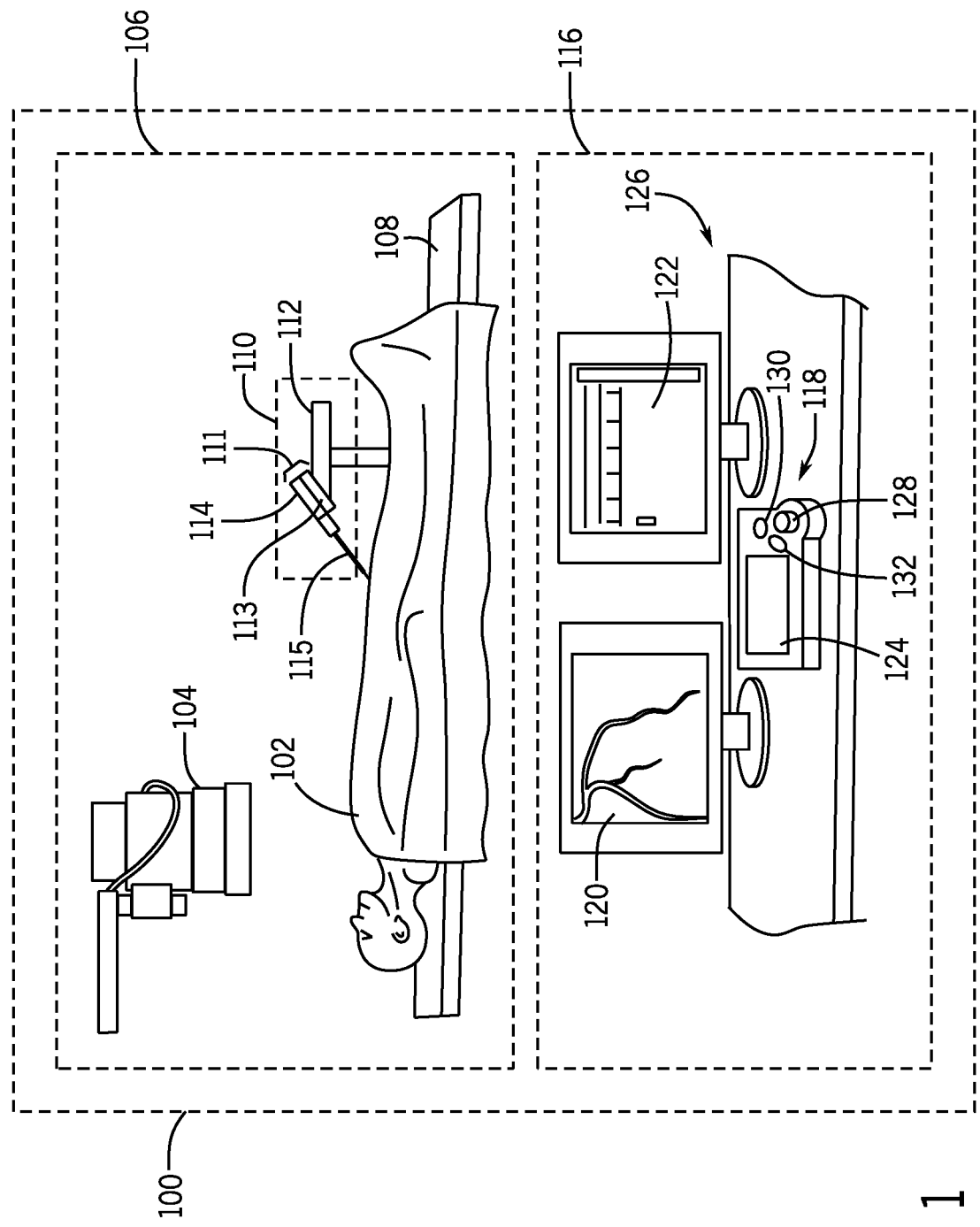
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures, e.g., percutaneous intervention procedure such as, a percutaneous coronary intervention (PCI), a neurovascular interventional procedure (e.g., to treat large vessel occlusion (LVO)), PCI for ST-segment elevation myocardial infarction, peripheral vascular intervention procedures, etc. Catheter based medical procedures may include diagnostic catheterization procedures during which one or more catheters (or other elongated medical devices) are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter (or other elongated medical device) is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 described herein are explained primarily in relation to the diagnosis and/or treatment of coronary disease, catheter procedure system 100 may be used to diagnose and/or treat any type of disease or condition amenable to diagnosis and/or treatment via a catheter-based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters such as balloon catheters and stent delivery system, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a drive assembly 111 supported by a robotic arm 112. The drive assembly 111 includes a cassette 114 mounted on a robotic drive 113 which may be used to drive an elongated medical device 115 such as a catheter or guide wire. For example, the drive assembly 111 may be used to automatically feed a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 2) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices (e.g., elongated medical devices) with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Drive assembly 111 includes various drive mechanisms to cause movement (e.g., axial and rotational movement) of the components of the bedside system 110 including the percutaneous intervention devices.

In one embodiment, controls 118 include a touch screen 124, one or more joysticks 128 and buttons 130, 132. The joystick 128 may be configured to advance, retract, or rotate various components and percutaneous intervention devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. In other embodiments, the user interface 126 may include one display or more than two displays. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 3). In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

Figure 2:
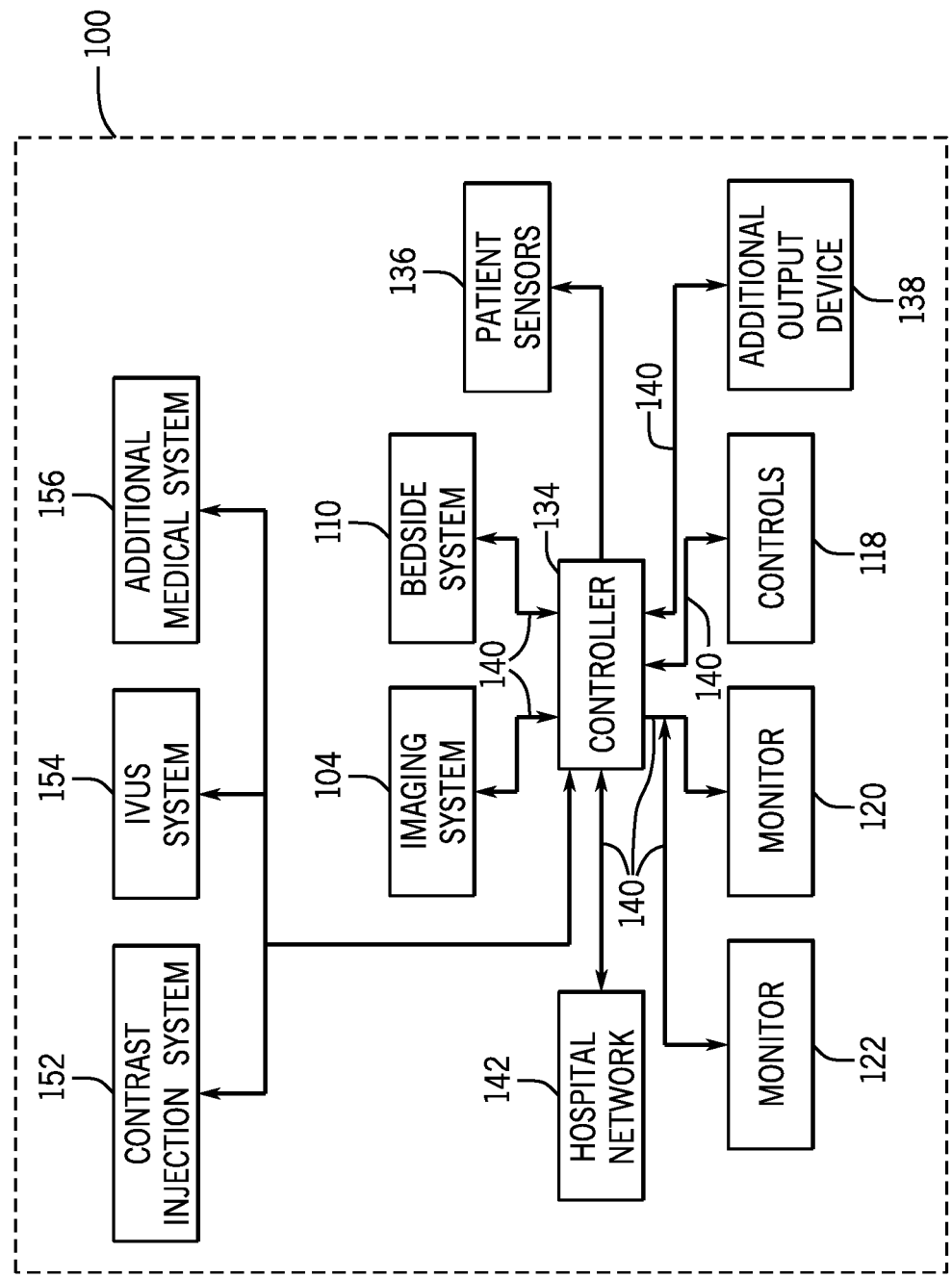
FIG. 2 is a schematic block diagram of an exemplary catheter procedure system in accordance with an embodiment.

Referring to FIG. 2, a block diagram of catheter procedure system 100 is shown according to an exemplary embodiment. Catheter procedure system 100 may include a controller 134. Controller 134 may be part of workstation 116 (shown in FIG. 1). Controller 134 may generally be an electronic control unit suitable to provide catheter procedure system 100 with the various functionalities described herein. For example, controller 134 may be an embedded system, a dedicated circuit, a general-purpose system programed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In an embodiment, controller 134 may also be in communication with a contrast injection system 152 and an intravascular ultrasound (IVUS) system 154. Controller 156 may also be in communication with other medical systems 156 such as, for example, an OCT system, an FFR system, or aspiration pump. In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include image processing engines, data storage and archive systems, automatic balloon and/or stent inflation systems, medicine injection systems, medicine tracking and/or logging systems, user logs, encryption systems, systems to restrict access or use of catheter procedure system 100, etc.

As mentioned, controller 134 is in communication with bedside system 110 and may provide control signals to the bedside system 110 to control the operation of the motors and drive mechanisms used to drive the percutaneous intervention devices (e.g., guide wire, catheter, etc.). The bedside system 110 may include, for example, a guide wire axial drive mechanism that provides for advancement and/or retraction of a guide wire, a working catheter axial drive mechanism that provides for advancement and/or retraction of a working catheter and a guide wire rotational drive mechanism that is configured to cause a guide wire to rotate about its longitudinal axis. In one embodiment, the various drive mechanism are housed in a drive assembly 114 (shown in FIG. 1).

Figure 3:
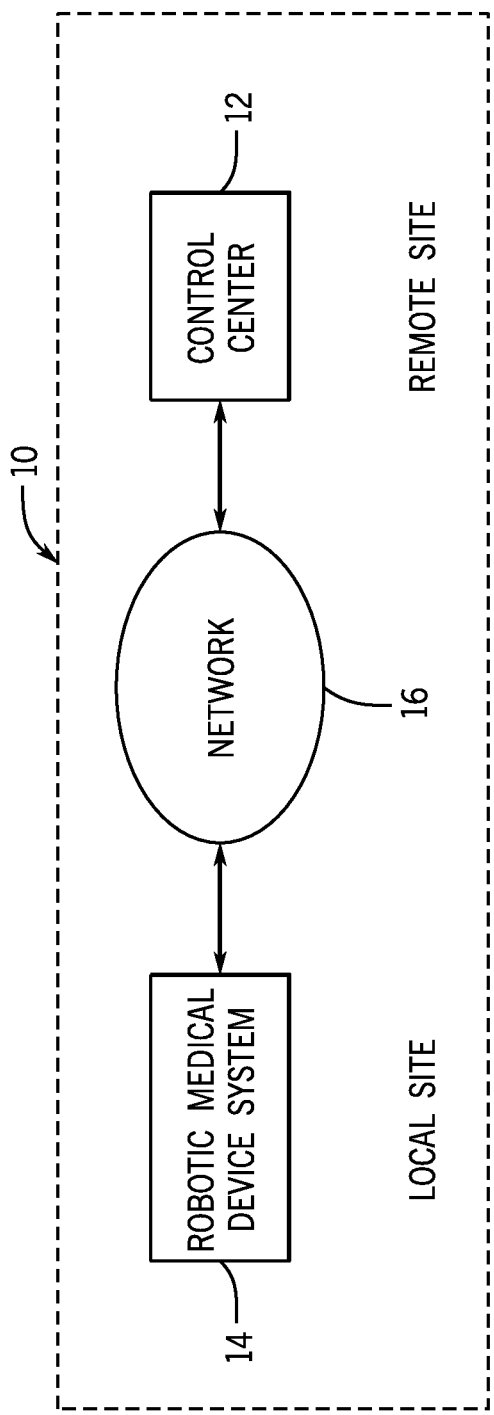
FIG. 3 is a block diagram of a communications and control system for a robotic medical device system in accordance with an embodiment.

A robotic medical device system such as the example catheter procedure system described above with respect to FIGS. 1 and 2 may be controlled remotely. FIG. 3 is a perspective view of a communications and control system for a robotic medical device system in accordance with an embodiment. The communication and control system 10 includes a control center 12 at a remote site or location and a robotic medical device system 14 at a local site or location. As used herein, the local site is the location of the robotic medical device system and a patient or subject and the remote site is the location of an operator (e.g., a doctor) and a control center used to control the robotic medical device system remotely. The control center 12 and the robotic medical device system 14 are in communication over a network 16 such as, for example, the Internet. In an embodiment, the remote site and the local site are away from one another, for example, different rooms in the same building, different buildings in the same city, different cities, or other different locations where the remote site does not have physical access to the robotic medical device system or patient at the local site. The control center 12 and robotic medical device system 14 communicate (e.g., data, images, command and control signals) over the network 16. An operator at the remote site may use the control center 12 to control and operate the robotic medical device system 14 at the local site to perform a medical procedure. In an embodiment, multiple control centers 12 may be in communication with one robotic medical device system 14 via network 16 and each control center 12 may be used to control the robotic medical device system 14 from a separate location. In another embodiment, multiple control centers 12 may be in communication with multiple robotic medical device systems 14 via network 16 where each of the control centers 12 may be used to control each of the robotic medical device systems 14.

The robotic medical device system 14 may be, for example, a catheter procedure system or other medical device system that may be robotically controlled to perform a procedure. In an embodiment, network 16 is a secure network such as, for example, a virtual private network. Control center 12 may include, for example, a workstation with a user interface. In one embodiment, the control center 12 includes a user interface that is similar to a user interface provided in the robotic medical device system 14. For example, if the robotic medical device system 14 is a catheter procedure system such as the system described above with respect to FIGS. 1 and 2, the control center 12 may include a workstation with a user interface and controls similar to the workstation 116, user interface 126 and controls 118 of the catheter procedure system 100. In another embodiment, the control center 12 includes a workstation or user interface that is part of a robotic medical device system at the remote site. The control center 12 is configured to allow an operator to operate various components of the robotic medical device system 14 from the remote site. Information such as data, images, and command and control signals are transmitted from the control center 12 over the network 16 to the robotic medical device system 14 and information such as data and images are transmitted from the robotic medical device system 14 over the network 16 to the control center 12.

Figure 4:
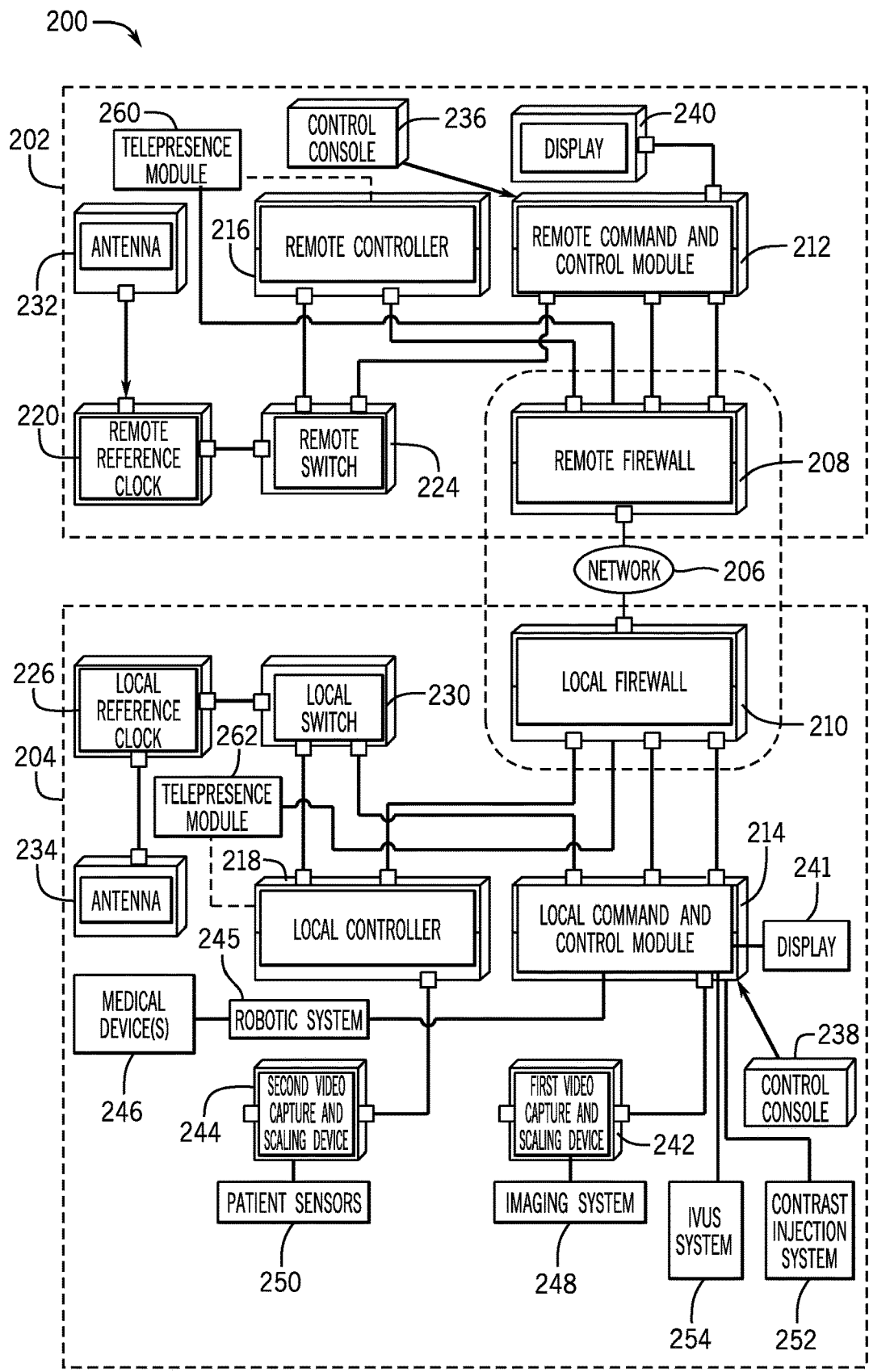
FIG. 4 is a block diagram of a communications and control system for a robotic medical device system in accordance with an embodiment.

FIG. 4 is a block diagram of a communications and control system for a robotic medical device system in accordance with an embodiment. The communications and control system 200 includes a control center 202 at a remote site and a robotic medical device system 204 at a local site. The control center 202 and the robotic medical device system 204 are in communication over a network 206. In an embodiment, the network 206 is a secure network established with a remote firewall 208 in the control center 202 and a local firewall 210 in the robotic medical device system 204. For example, the network 206 may be a virtual private network (VPN). The network 206 is configured to receive and transmit data, images, and command and control signals. In the system 200 shown in FIG. 4, one control center 202 and one robotic medical device system 204 are shown. In an embodiment, multiple control centers 202 may be in communication with one robotic medical device system 204 via network 206 and each control center 202 may be used to control one or more medical devices 246 using a robotic system 245 in the robotic medical device system 204 from a separate location. The robotic system 245 may be, for example, a robotic arm, a robotic drive and/or other robotic device that can be used to drive a medical device. In an embodiment where the robotic medical device system is a catheter system, the robotic system 245 may be a robotic arm 112 and a drive assembly 111 as described above with respect to FIG. 1. In another embodiment, multiple control centers 202 may be in communication with multiple robotic medical device systems 204 via network 206 where each of the control centers 202 may be used to control one or more medical devices 246 using a robotic system 245 in each of the robotic medical device systems 204.

Control center 202 also includes a remote command and control module 212 and a remote controller 216 coupled to and in communication with the remote firewall 208. In one embodiment, the remote firewall 208, the remote command and control module 212 and the remote controller 216 are implemented on separate hardware (e.g., computer systems). In another embodiment, the remote firewall 208, the remote command and control module 212 and the remote controller 216 are implemented as separate software components or logical subsystem components on the same computer system. The software components or logical subsystem components may be achieved using, for example, microkernels, virtual machines, or conventional operating systems with real time extensions. In another embodiment, the remote controller 216 and the remote firewall 208 may be implemented as a software programs executing on the remote command and control module 212. The remote command and control module 212 receives command and control signals from a control center control console 236. The control console 236 is configured to receive user inputs from an operator at the remote site for the operation of the robotic medical device system 204 and other systems and devices at the local sites. For example, control console 236 may include a display and controls such as a touch screen, one or more joysticks and buttons. A first display 240 in the control center 202 is coupled to the remote command and control module 212 and may be used to display data and images received from the robotic medical device system 204. Remote command and control module 212 may be configured to decompress images received from the robotic medical device system 204.

Remote command and control module 212 is also coupled to a time synchronization reference clock such as, for example, a remote reference clock 220 and receives time information from the remote reference clock 220. The remote reference clock 220 may be, for example, a grandmaster clock. As discussed further below, the time information may be used to calculate delays in the transmission of signals and data (e.g., command and control signals, and images) between the remote site and the local site. The remote reference clock 220 is coupled to an antenna 232 to receive time information from an external time source such as, for example, a satellite-based time source or an external network and to provide timestamp information to the remote command and control module 212. In one embodiment, the time information is provided from a global positioning system (GPS). In another embodiment, the time information is provided from a satellite time and location (STL) system. A remote switch 224 may be coupled to the remote reference clock 220. In an embodiment, the remote reference clock 220, the remote switch 224 and the remote command and control module 212 use a precision time protocol (PTP) network. Remote command and control module 212 uses the timestamp information from the remote reference clock 220 to timestamp the command and control signals received from the control console 236. The timestamped command and control signals may be transmitted via network 206 to a local command and control module 214 in the robotic medical device system 204. The local command and control module 214 is configured to provide the command and control signals over network 206 to, for example, a robotic system 245 in the robotic medical device system 204 to control the operation of the medical device(s) 246. The timestamp provided on the command and control signals by the remote command and control module 212 based on the information from the remote reference clock 220 may be used to monitor and control delays in the transmission of the command and control signals over the network 206 during a medical procedure performed using the medical device(s) 246. The local command and control module 214 is configured to determine the delay in receiving the command and control signals from the control center 202 based on the timestamps and to take appropriate action based on the amount of delay, as discussed further below with respect to FIG. 5.

The local command and control module 214 and the local controller 218 are coupled to and in communication with the local firewall 210. In one embodiment, the local firewall 210, the local command and control module 214 and the local controller 218 are implemented on separate hardware (e.g., computer systems). In another embodiment, the local firewall 210, the local command and control module 214 and the local controller 218 are implemented as separate software components or logical subsystem components on the same computer system. The software components or logical subsystem components may be achieved using, for example, microkernels, virtual machines, or conventional operating systems with real time extensions. In another embodiment, the local controller 218 and local firewall 210 may be implemented as a software programs executing on the local command and control module 214. The local command and control module 214 may also receive command and control signals from a robotic medical device system control console 238. The control console 238 is configured to receive user inputs from an operator at the local site for the operation of the robotic medical device system 204 at the local site. For example, control console 238 may include a display and controls such as a touch screen, one or more joysticks and buttons. A display 241 is coupled to the local command and control module 214 and may be used to display data and images. Local command and control module 214 also receive images from an imaging system 248 and hemodynamic data from patient sensors 250. In an embodiment where the robotic medical device system 204 is a catheter procedure system as described above with respect to FIGS. 2 and 3, the local controller 218 may be coupled to a display 120, 122 or touch screen 124. The images from imaging system 248 may be captured and scaled using a first video capture and scaling device 242 and the hemodynamic data may be captured and scaled using a second video capture and scaling device 244. Local command and control module 214 may be configured to compress the image data before transmission to the control center 202 and local controller 218 may be configured to compress the hemodynamic data before transmission to the control center 202. In another embodiment, the local command and control module 214 is coupled to and receives data from an intravascular ultrasound (IVUS) system 254. Data from the IVUS system 254 may be transmitted to control center 202.

The local command and control module 214 is also coupled to a time synchronization reference clock such as, for example, a local reference clock 226 and receives time information from the local reference clock 226. The local reference clock may be, for example, a grandmaster clock. The time information may be used to calculate delays in the transmission of signals and data (e.g., command and control signals, and images) between the remote site and the local site. The local reference clock 226 is coupled to an antenna 234 to receive time information from an external time source such as, for example, a satellite-based time source and to provide timestamp information to the local command and control module 214. In one embodiment, the time information is provided from a global positioning system (GPS). In another embodiment, the time information is provided from a satellite time and location (STL) system. A local switch 230 may be coupled to the local reference clock 226. In an embodiment, the local reference clock 226, the local switch 230 and the local command and control module 212 use a precision time protocol network. Local command and control module 214 uses the timestamp information from the local reference clock 226 to timestamp the image data received from the first video capture and scaling device 242. In another embodiment, the local controller 218 may use the timestamp information from the local reference clock 226 to timestamp the hemodynamic data received from the second video capture and scaling device 244. The timestamped images and hemodynamic data may be transmitted via network 206 to the remote command and control module 212 in the control center 202. The remote command and control module 212 is configured to provide the images to a display 240 in the control center 202 and the hemodynamic data to display 240 or another display in the control center 202. The timestamp provided on the images and hemodynamic data by the local command and control module 214 based on the information from the local reference clock 226 may be used to monitor and control delays in the transmission of the images and hemodynamic data over the network 206 during a medical procedure performed using the control center 202 to control the robotic system 245 and the medical device(s) 246. Various components of the system 200 may be paused or halted or control of the system passed between the control center 202 and the robotic medical device system 204 based on the delay in transmission of the images and/or hemodynamic data.

As described above, the control center 202 may include a remote reference clock 220 that may us a precision time protocol and the robotic medical device system 204 includes a local reference clock 226 that may use a precision time protocol. The remote reference clock 220 and local reference clock 226 may be in communication with a common external time source, for example, a satellite-based time source such as GPS or STL to receive time information. This embodiment advantageously enables the control center 202 and the robotic medical device system 204 to communicate over a secure tunnel on a network 206 (e.g., the Internet) and compute the command delay and round trip delay in order to ensure safe secure operations. Each site uses a dedicated reference clock (e.g., reference clock 220, 226, respectively) and an isolated Ethernet network for time synchronization. Either the NTP (Network Time Protocol) or the PTP may be used for synchronization in this embodiment. However, the PTP network may allow for better synchronization than NTP. Another advantage of using a dedicated reference clock at each site over an isolated network is to eliminate an attack surface for network attacks aimed at time references which are made accessible to the Internet. Such vulnerabilities include, but are not limited to, denial of service (DoS) which render the GMC unavailable, and stack overflow which render the command and control module under the control of an adversary. As discussed further below with respect to FIG. 16, in an embodiment firewalls may be used to establish an IPSec encrypted tunnel with dedicated hardware between two nodes with privately held keys for high levels of security and minimal delay impact on communications.

In another embodiment, the control center 202 and the robotic medical device system 204 may not include their own reference clock. Rather, the control center 202 ad the robotic medical device system 204 are configured to utilize a NTP and are in communication with a single network grandmaster clock to received time information. As mentioned above, the time information may be used to generate timestamps for command and control signals and other data (e.g., images and hemodynamic data). In one embodiment, the timestamps are provided by a common time source (e.g., GPS or STL) to determine the delay in transmission of the sum of the command and control signals. In another embodiment, the timestamps are provided by a single time source (e.g., a network grandmaster clock or an internal clock) to determine the delay in the transmission of the sum of the command and control signals. In this embodiment, the timestamp from the "remote" site would be used and then the roundtrip command and control signal and image delay would be computed when the timestamp is received back from the image transmission from the "local" site.

As mentioned above, the control center 202 may be used by an operator at the remote site to operate and control the robotic medical device system 204 and other systems and devices at the local site. In an embodiment, the control center 202 may provide command and control signals over the network 206 to imaging system 248 or a contrast delivery system 252. For example, control center 202 may be used to control image capture by the imaging system 248. In another example, control center 202 may be used to control contrast injection by contrast injection system 252. In other examples, control center 202 may be used to control the actuation of an aspiration pump or the deployment of a stent retriever.

Control center 202 incudes a telepresence module 260 and the robotic medical device system 204 includes a telepresence module 262. Each telepresence module 260, 262 is configured to provide audio and video communication (e.g., telepresence, teleconference) between an operator at the remote site and a user or local staff at the local site. In one embodiment, as shown in FIG. 4, telepresence modules 260, 262 are standalone modules and may be coupled to the remote firewall 208 and local firewall 210, respectively. In another embodiment, elements of the telepresence modules 260, 262 may be a software program executing on the remote controller 216 or the local controller 218, respectively. Telepresence modules 260 and 262 may include, for example, a video camera, monitors, speakers and microphone(s). In one embodiment, a video conference may be established between telepresence module 260 at the remote site and the telepresence module 262 at the local site so that the operator at the remote site utilizing the control center 202 to operate the medical device(s) 246 using the robotic system 245 at the local site may view the procedure room and equipment as the procedure is performed and communicate via audio and video with personnel (e.g., as technician, a physician, etc.) supporting the procedure at the local site. In an embodiment, audio and video communication may be established between the telepresence module 260 at the remote site and the telepresence module 262 at the local site using a dedicated audio and video communication system which establishes secure communication over a computer network (e.g., a cloud network). For example, the telepresence module 260 at the remote site may be configured to transmit the audio (e.g., speech) and video from the remote site in an encrypted format (e.g., SRTP/AES-128) and configured to receive and decrypt audio (e.g., speech) and video from the telepresence module 262 at the local site. The telepresence module 262 at the local site may be configured to transmit the audio (e.g., speech) and video from the local site in an encrypted format (e.g., SRTP/AES-128) and configured to receive and decrypt audio (e.g., speech) and video from the telepresence module 260 at the remote site. Signaling and routing between the telepresence module 260 and the telepresence module 262 may be established using a cloud network. In an embodiment, the encrypted audio and video data may be transmitted between the remote firewall 208 and the local firewall 210 without further encryption (e.g., the audio and video data may be whitelisted).

Figure 5:
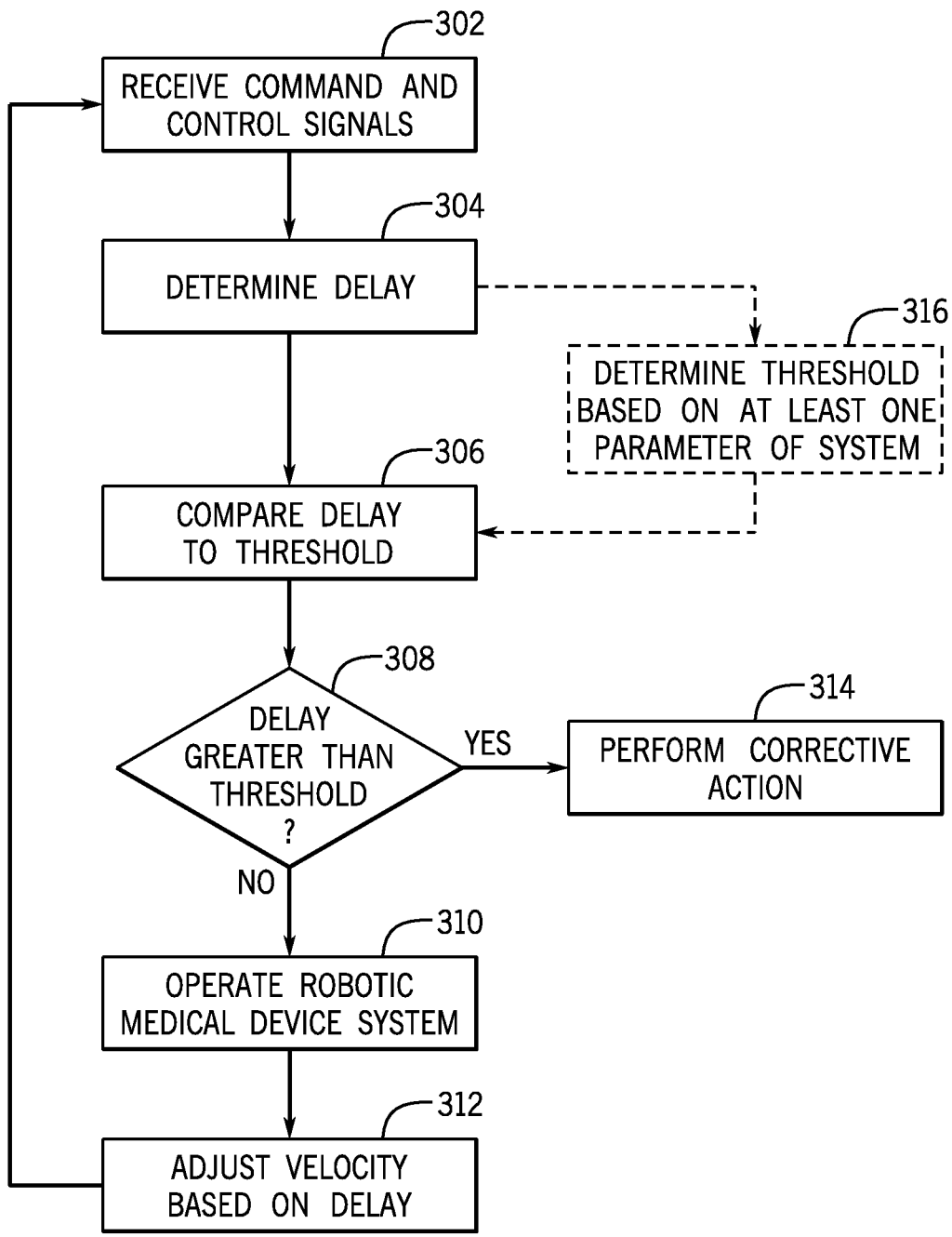
FIG. 5 illustrates a method for controlling operation of a robotic medical device system in accordance with an embodiment.

FIG. 5 illustrates a method for controlling operation of a robotic medical device system in accordance with an embodiment. Referring to FIGS. 4 and 5, at block 302 command and control signals are received by, for example, the local command and control module 214 at the local site from the control center 202 at the remote site. At block 304, the delay in receiving the command and control signals is determined, for example, by the local command and control module 214 based on the timestamp information. At block 306, the delay is compared to a threshold value. In one embodiment, the threshold is a predetermined value, for example, based on what is perceptible to a user such as 250 ms. In another embodiment discussed further below, the threshold is determined at block 316 based on at least one parameter of the robotic medical device system, for example, the procedure being performed by the robotic medical device system, patient anatomy, type of medical device, and location of the medical device. At block 308, if the delay is greater than the threshold corrective action may be performed at block 314. In one embodiment, the medical device(s) 246 and other components of the system 204 may be paused or stopped. In one example of a pause, if the delay is greater than the threshold value and then the delay goes below the threshold, the device or component may be paused and then start moving again once the delay goes above the threshold value. In another example, if the delay is too large, the movement of the device or component may be paused until the delay becomes low enough to resume operation. In another embodiment, the speed or velocity (e.g., during advancement, retraction or rotation) of components of the robotic medical device system may be slowed down. If the network connection has been lost or the speed of the network 206 has slowed below a predetermined rate, the control center 202 may give control of the robotic system 245 and the medical device(s) 246 back to the robotic medical device system 204. An emergency stop may also be provided so that a user at the local site may stop the procedure for an emergency. In an embodiment, the threshold is a range of threshold values. If the control center 202 has control of the robotic system 245 and the medical device(s) 246 and the delay of the command and control signals is greater than a first threshold and less than a second threshold, the control console 236 (e.g., a joystick) of the control center 202 may be disabled but the control console 236 maintains control of the robotic system 245 and the medical device(s) 246. If the control center 202 has control of the robotic system 245 and the medical device(s) 246 and the delay of the command and control signals is greater than the second threshold, then the control center 202 may be disabled.

At block 308, when the control center 202 has control of the robotic system 245 and the medical device(s) 246 if the delay of the command and control signals is less than the threshold, the control console 236 of control center 202 may be used to control and operate the robotic medical device system 204 including the robotic system 245 and the medical device(s) 246 at block 310. At block 312, the velocity of the medical device 246 as it is being controlled by the control center 202 may be adjusted based on the delay of the command and control signals. If the control center 202 has control of the robotic system 245 and the medical device 246 and the delay ($t_{delay}$) of the command and control signals is less than a predetermined amount ($t_{predetermined}$) and greater than zero, the commanded velocity ($v_{command}$) from the command and control signals received from the control console 236 (e.g., a joystick) is scaled so that the velocity of the device 246 ($v_{device}$) decreases as the delay increases towards the predetermined amount. The velocity of the device may be given by:

$$v_{device} = v_{command} \times \max(t_{predetermined} - t_{delay}, 0) / t_{predetermined} \quad (1)$$

For example, if the delay, $t_{delay}$, is equal to half of the predetermined amount, $t_{predetermined}$, then the velocity of the device, $v_{device}$, will half of the command velocity, $v_{command}$. Slowing the device 246 down as delay, $t_{delay}$, increases may be used to ensure stability of the system and mitigate risk associated with device control, for example, to avoid advancing or retracting the device excessively. If the delay, $t_{delay}$, is greater than the predetermine amount, $t_{predetermined}$ (block 308), then the velocity of the device, $v_{device}$, is zero and movement of the device 246 is stopped (block 314). In another embodiment, the velocity of the device, $v_{device}$, may be adjusted based on the total network delay. The total network delay includes the delay of the command and control signals, $t_{delay}$, and the delay of images received from the robotic medical device system 204, $t_{imagedelay}$. The velocity of the device may be given by:

$$v_{device} = v_{command} \max(t_{predetermined} - (t_{delay} + t_{imagedelay}), 0) / t_{predetermined} \qquad (2)$$

Scaling the command velocity ($v_{command}$) of the device based on the total network delay $t_{total} = (t_{delay} + t_{imagedelay})$ may ensure stable operation and robust performance for positional control of the device. The various embodiments for scaling the command velocity given above may be tuned to ensure stability despite any total delay. If the delay is unknown, instabilities may occur if the delay is too large. The frequency response for the open loop system under fixed total delay may be given as follows:

$$H(j\omega) = \frac{1}{\omega} e^{-j(\frac{\pi}{2} + \omega t_{total})} \qquad (3)$$

From the Nyquist stability criteria, in order for stability to be ensured for unity proportional feedback, the total network delay needs to satisfy the following constraint:

$$t_{total} \leq \frac{\pi}{2} \text{ seconds.}$$

Using the scaling in equation (2) above, in which $$t_{predetermined} = \frac{\pi}{2},$$

results in the frequency response:

$$H(j\omega) = \frac{\frac{\pi}{2} - t_{total}}{\frac{\pi}{2}\omega} e^{-j(\frac{\pi}{2} + \omega t_{total})} \qquad (4)$$

In other embodiments, other optimal values for $t_{predetermined}$ may be calculated and used in the scaling of equation (2). From equation (4), the stability may be ensured for proportional unity feedback as the gain margin is now infinity for unity proportional feedback. Other methods may be used in a similar manner with the knowledge of the feedback delay to ensure stability. An example of an approach to use wave variables to ensure stability without knowledge of the feedback delay as well when using velocity commands to control the position of the device is described in "Design of Networked Control Systems Using Passivity," N. Kottenstette, J. F. Hall, X. Koutsoukos, J. Sztipanovits and P. Antsaklis, IEEE Transactions on Control Systems Technology, vol. 21, no. 3, pp. 649-665, May 2013, herein incorporated by reference in its entirety.

As mentioned above, at block 316, the delay threshold may be determined based on at least one parameter of the robotic medical device system 204 including, for example, the procedure being performed by the robotic medical device system. For example, the robotic medical device system 204 may be a catheter procedure system that controls the movement and operation of elongated medical devices (e.g., catheters, guidewires, balloon catheters, microcatheters, etc.). The amount of delay that is acceptable may vary depending on various parameters of the catheter procedure system. The value of the delay threshold (i.e., the acceptable amount of delay) may be based on, for example, the type of procedure being performed, the patient anatomy, the type of elongated medical device (e.g., catheter, balloon catheter, guide catheter, guidewire, microcatheter), the location of the elongated medical device, the distance between the elongated medical device (e.g., the tip or distal end of the device) and a target location, or the type of movement begin performed by the elongated medical device (e., advancement, rotation, retraction). For example, more delay may be tolerated when the elongated medical device (e.g., the tip of the elongated medical device) is further away from the target location, when the elongated medical device is being retracted or if the elongated medical device is a device that travels on a wire (e.g., a microcatheter or balloon catheter) or a guidewire.

Figure 6:
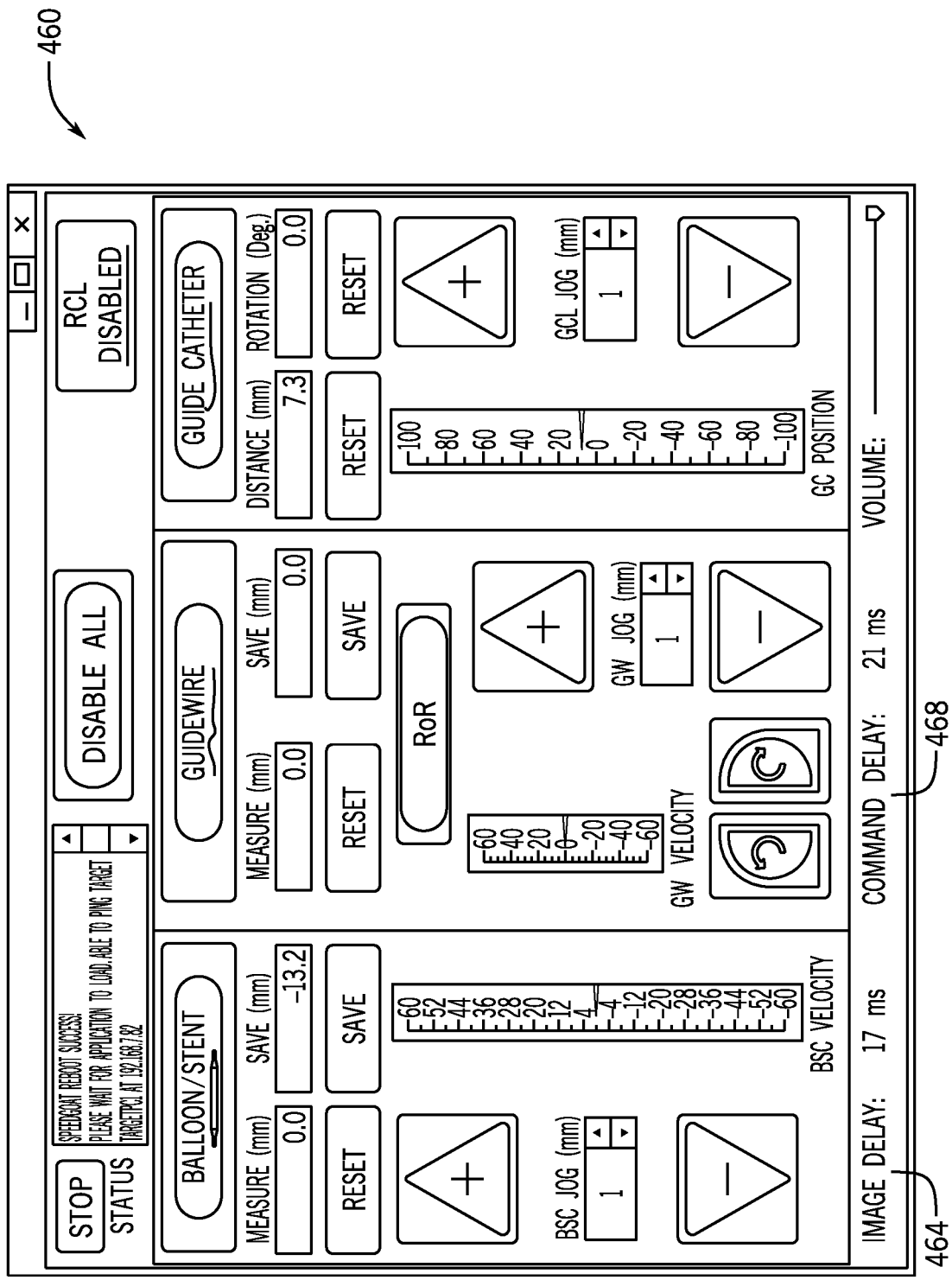
FIG. 6 shows an exemplary graphical user interface for a control center in accordance with an embodiment.
Figure 7:
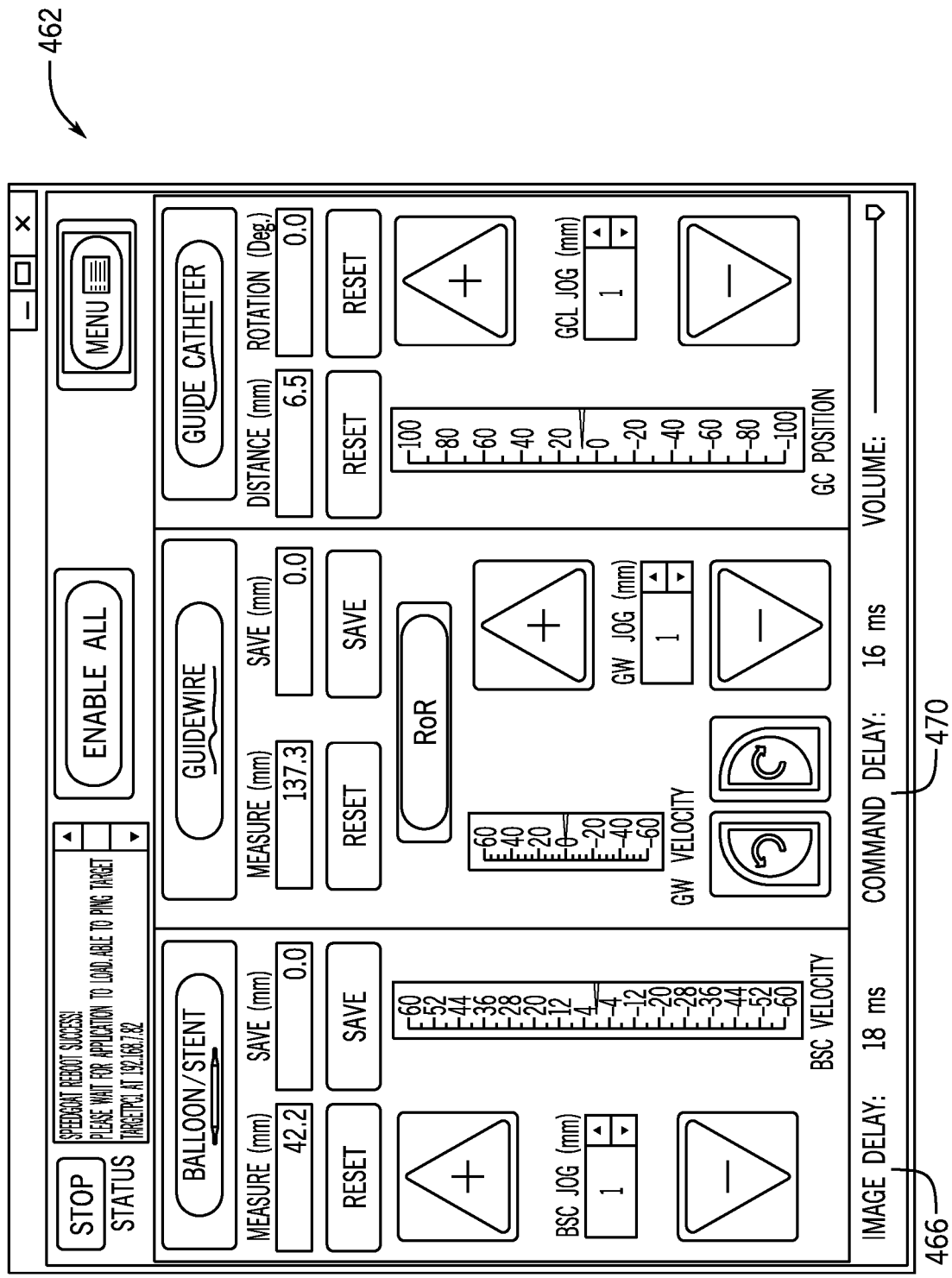
FIG. 7 shows an exemplary graphical user interface for a robotic medical device system in accordance with an embodiment.

In an embodiment, the remote controller 216 (shown in FIG. 4) and the local controller 218 (shown in FIG. 4) each generate and display a similar graphical user interface. FIG. 6 shows an exemplary graphical user interface for a control center in accordance with an embodiment and FIG. 7 shows an exemplary graphical user interface for a robotic medical device system in accordance with an embodiment. In FIGS. 6 and 7, the graphical user interfaces 460, 462 shown are for control of an exemplary catheter procedure system. The graphical user interface 460 for a control center and the graphical user interface 462 for a robotic medical device system are configured to show, for example, the same measurements, velocities, saved settings and which control of a control console is being actuated at the active site (i.e., either the control center at the remote site or the robotic medical device system at the local site). Each graphical user interface 460, 462 displays the delay 464, 466 of the transmitted images from the robotic medical device system to the control console and the delay 468, 470 of the command and control signals from the control center to the robotic medical device system.

Figure 8:
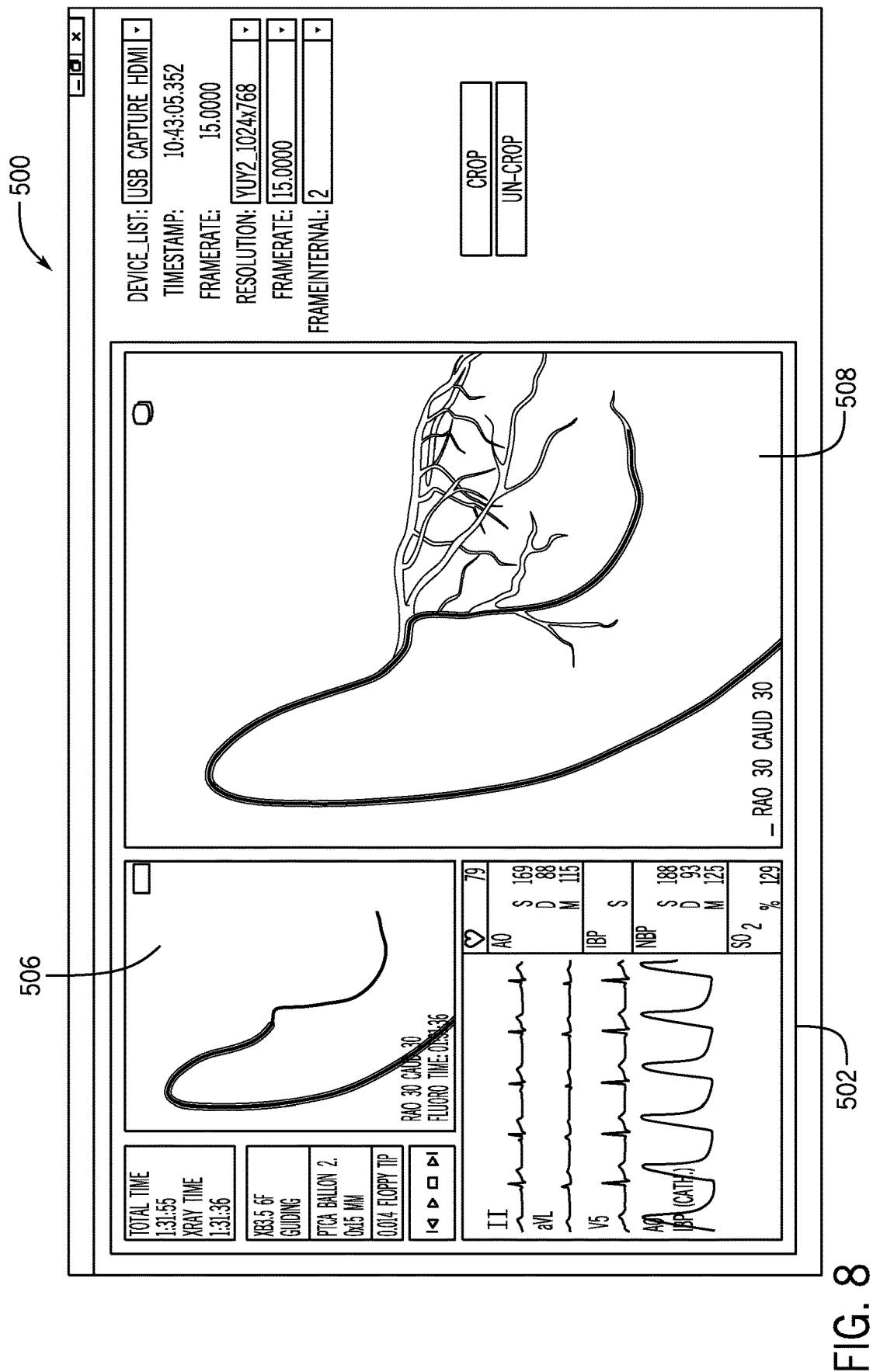
FIG. 8 shows an exemplary display of data and images for the robotic medical device system at the local site in accordance with an embodiment.
Figure 9:
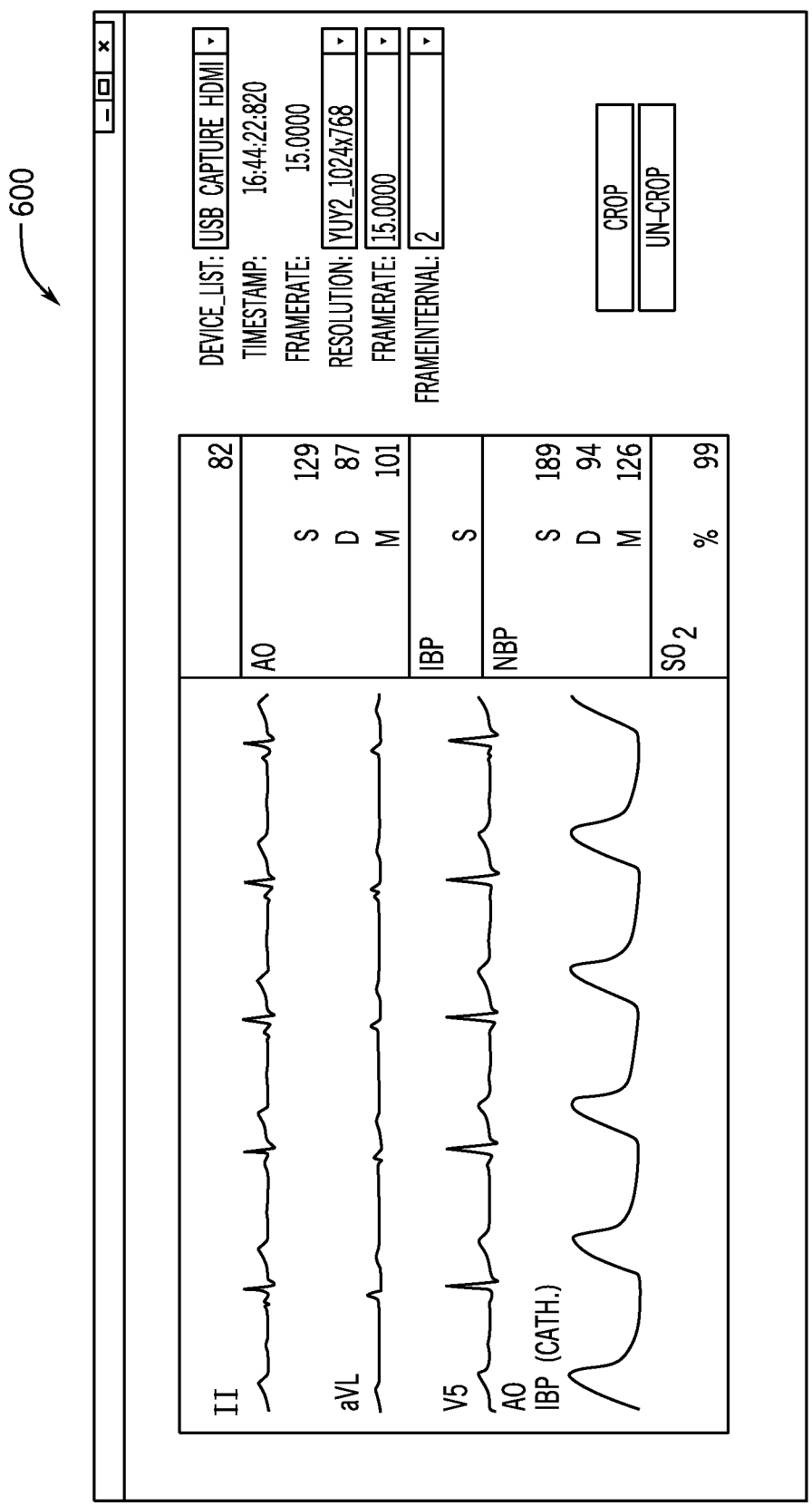
FIG. 9 shows an exemplary display for the control center at the remote site having hemodynamic data in accordance with an embodiment.
Figure 10:
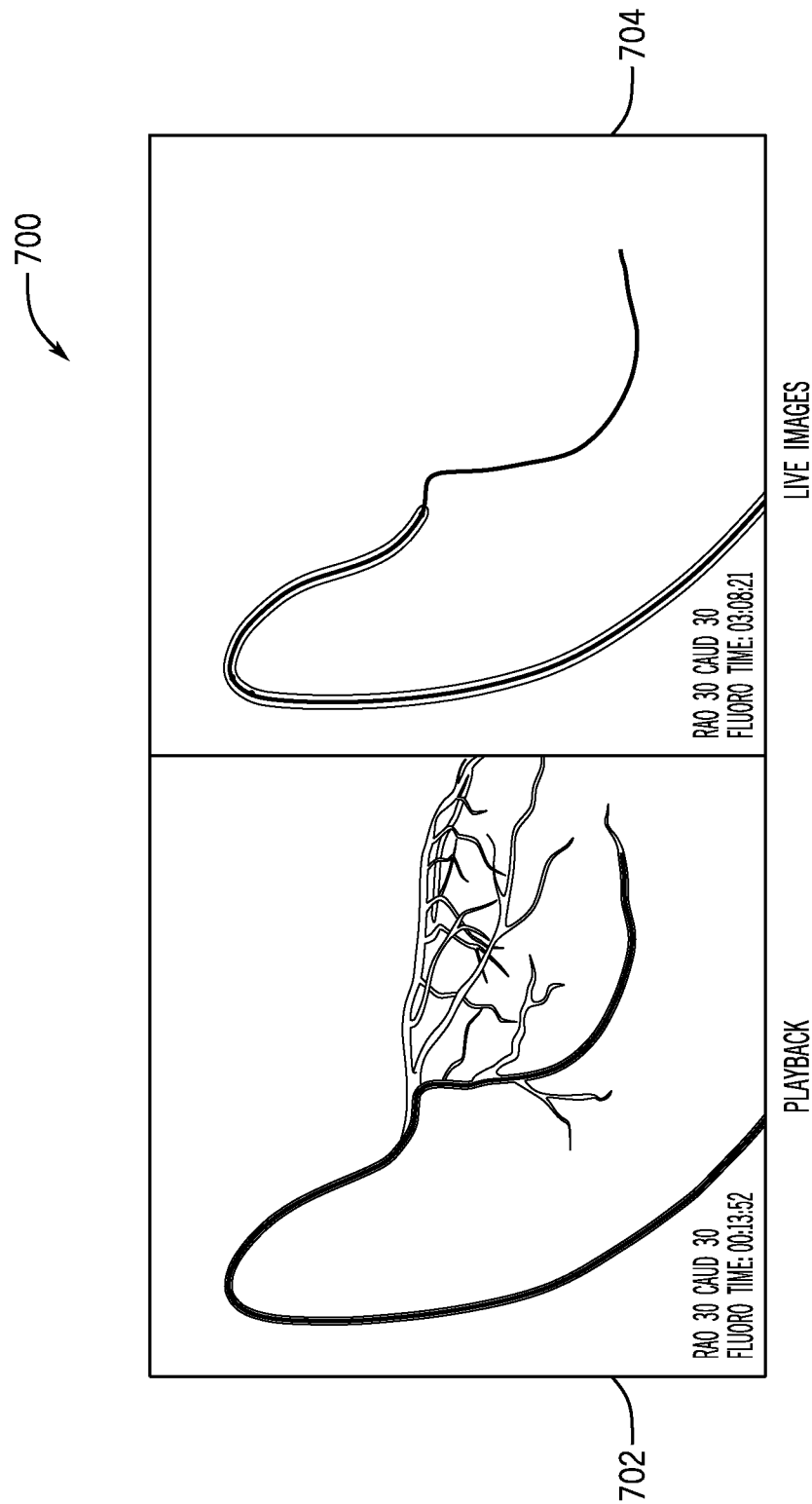
FIG. 10 shows an exemplary display for the control center at the remote site in accordance with an embodiment.

As discussed above with respect to FIG. 4, a display 240 of the control center 202 may be used to display data and images received from the robotic medical device system 204 over network 206. FIG. 8 shows an exemplary display of data and images for the robotic medical device system in accordance with an embodiment. The display 500 includes data and images captured at the robotic medical device system 204, such as, for example, hemodynamic data 502, a reference image 506 and a live image 508 related to the operation of a robotic medical device to perform a procedure. In particular, in the embodiment shown in FIG. 8, the data and images relate to a catheter procedure. The robotic medical device system 204 may be configured to select a section or region of interest of the display 500 for transmission to the control center 202 at the remote site. Accordingly, the display 500 may be cropped so that, for example, the hemodynamic data 502, reference image 506 and live image 508 may be transmitted separately. The selected section or region of interest may have any shape to capture the desired information for transmission. Cropping the display 500 may reduce the bandwidth required to transmit the images and data. FIG. 9 shows an exemplary display for the control center at the remote site having a selected region of interest including hemodynamic data in accordance with an embodiment. In FIG. 9, a display 600 includes hemodynamic data received from the robotic medical device system 204. In another embodiment, the remote controller 216 and display 240 may be configured to allow an operator to selectively circular buffer up to a predetermined time (e.g., 10 seconds) of the live image data (e.g., a fluoroscopic image data for a catheter procedure) as shown in FIG. 10. For example, a user may actuate a control to start the capture and create the circular buffer for the predetermined time for playback. In the embodiment shown in FIG. 10, the playback image shown in the display 700 is scaled to be the same scale as the live image 704. The playback 702 may be in real-time at a predetermined frames per second. In one embodiment, controls are provided that allow an operator to pause, step forward and step back through the playback image 702. The playback image may be used to, for example, facilitate generation of roadmaps and capture progression of the case.

Figure 14:
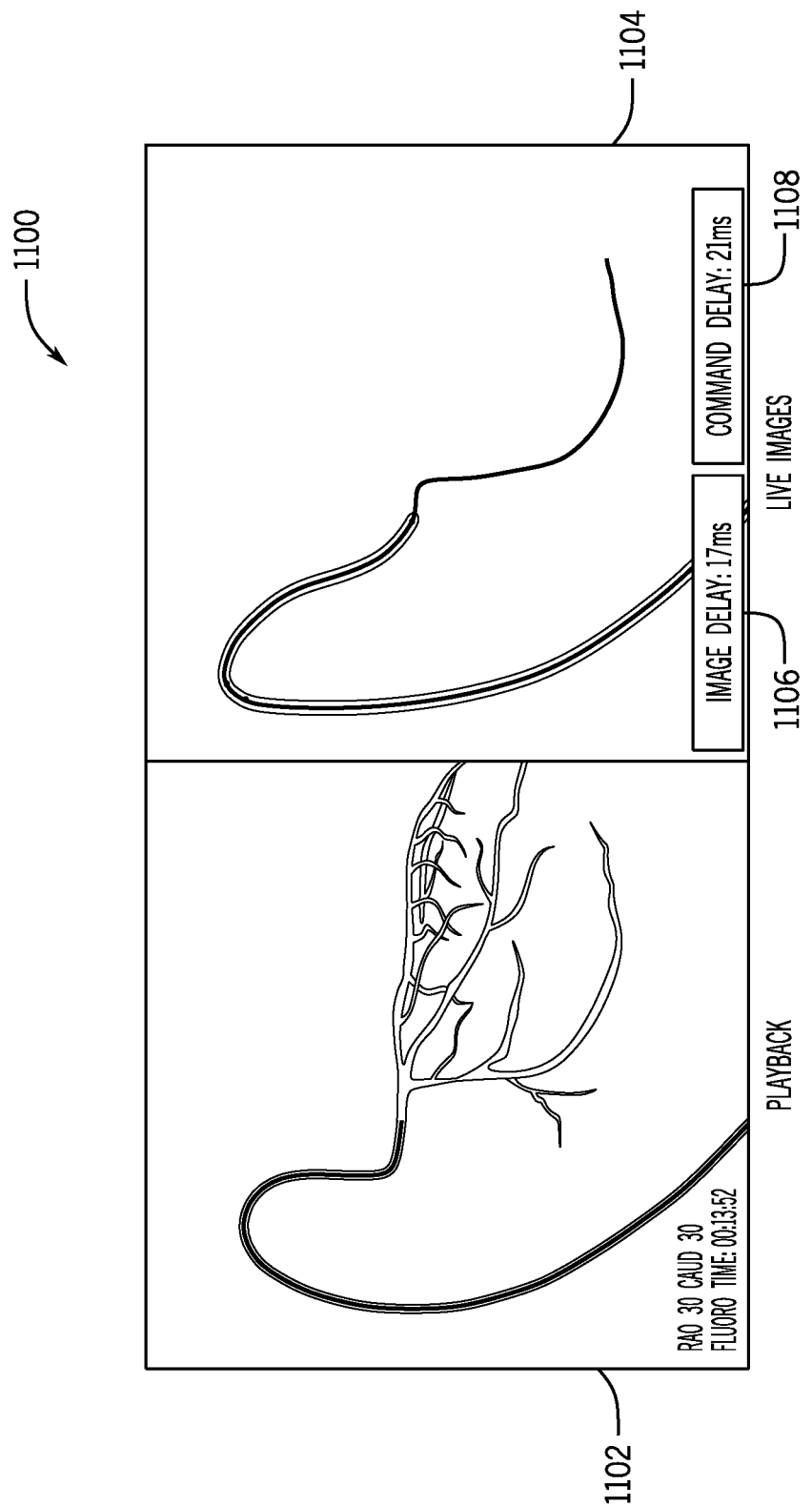
FIG. 14 shows an exemplary display for the control center at the remote site in accordance with an embodiment.
Figure 15:
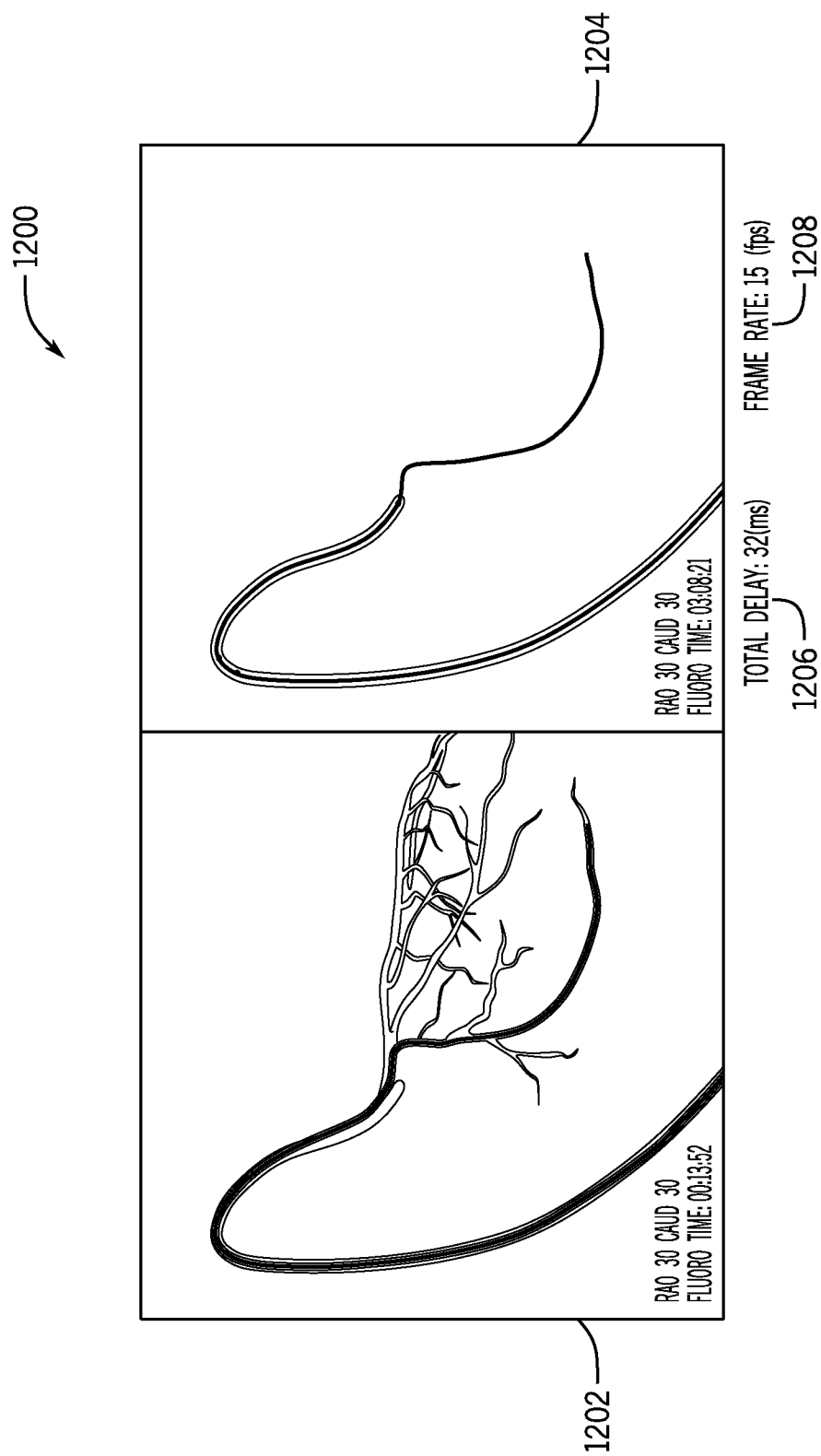
FIG. 15 shows an exemplary display for the control center at the remote site in accordance with an embodiment.

In another embodiment, a display of images at the remote site (e.g., on display 240 shown in FIG. 4) may be configured to display the image delay time and the command and control signal delay time as shown in FIG. 14. In FIG. 14, a display 1100 includes a playback image 1102 and a live image 1104. The display of the live image includes a display of the delay 1106 of the transmitted images from the robotic medical device system to the control console and the delay 1108 of the command and control signals from the control center to the robotic medical device system. In another embodiment, a display of images at the remote site (e.g., on display 240 shown in FIG. 4) may be configured to display the total delay as shown in FIG. 15. The total delay is the sum of the image delay time and the command and control signal delay time. In FIG. 15, a display 1200 includes a playback image 1202 and a live image 1204 which can include additional live information about the procedure such as the total delay and a frames rate for the images acquired by an imaging system associated with the robotic medical device system 204 at the local site. In an embodiment, the playback image 1202 may be scrolled to a region of interest after the image is captured. The display of the live image 1204 includes a display of the total delay 1206 and the frames rate 1208. The frames rate 1208 may be computed in terms of received frames per second. The total delay 1206 and the frames rate 1208 may be updated in real-time and/or be filtered to an appropriate bandwidth in order to improve the perception for the viewer of these values.

Figure 11:
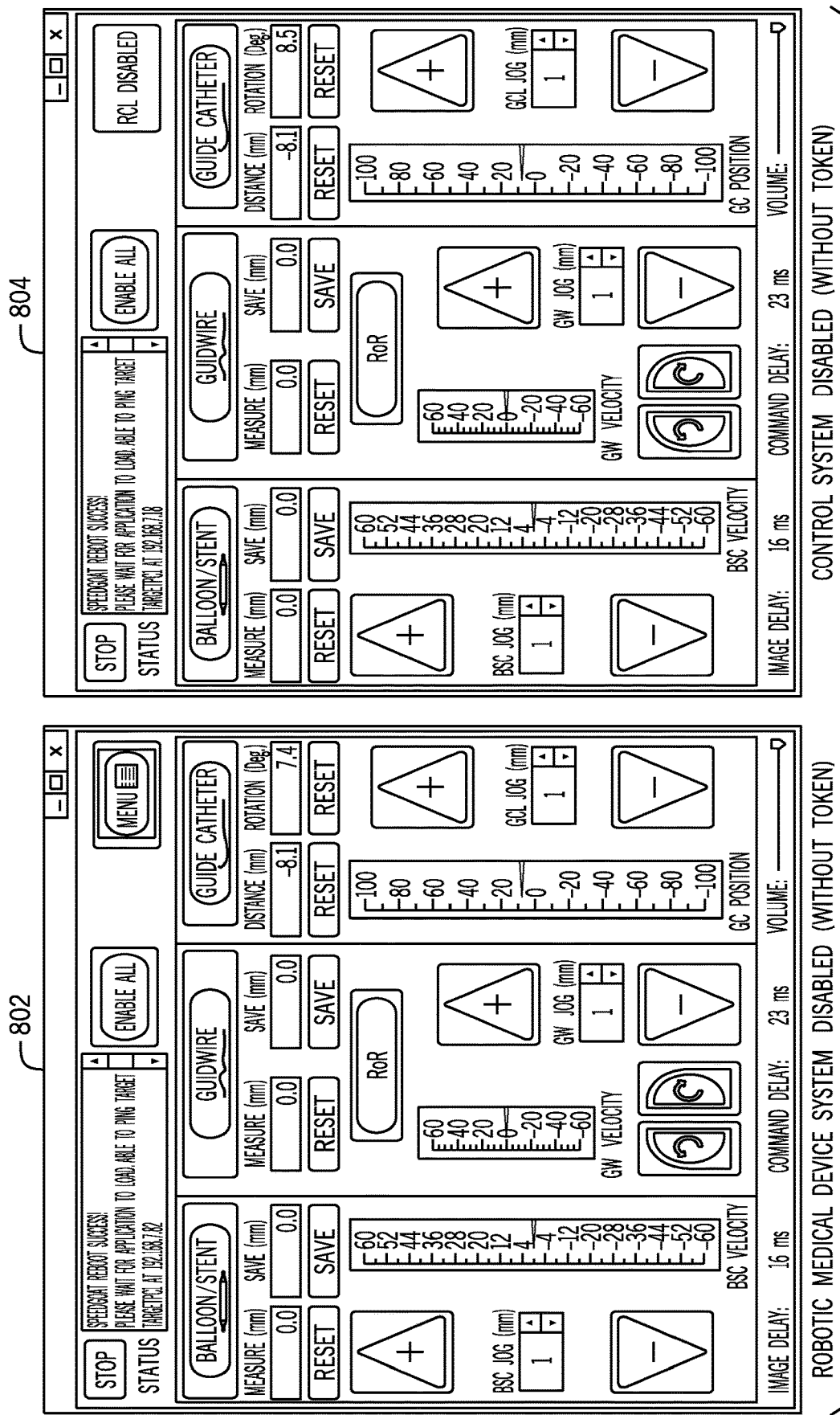
FIG. 11 shows exemplary user interfaces when neither the control center or robotic medical device system is in control of the robotic medical device in accordance with an embodiment.

As mentioned above with respect to FIG. 4, the communications and control system 200 is configured to allow an operator (e.g., a physician) at the remote site to control and operate the robotic medical device system 204 at the local site. The system 200 is also configured to allow an operator at the local site to control and operate the robotic medical device system 204. A control management process is provided to manage whether the control center 202 or the robotic medical device system 204 has control of the robotic system 245 and the medical device(s) 246. The control management system is configured to, for example, prevent deadlock between the remote site and the local site. In an embodiment, a control token is used to determine whether the control center 202 or the robotic medical device system 204 has control of operations to perform a procedure. The control token is a virtual token implemented in software. The system (e.g., either the control center 202 or the robotic medical device system 204) that has possession of the control token is given control of the robotic system 245 and the medical device(s) 246 of the robotic medical device system 204 and the other system is disabled and prevented from controlling the robotic system 245 ad the medical device(s) 246. In a first state, the control token is "free" and is available to be taken by either the control center 202 or the robotic medical device system 204. FIG. 11 shows exemplary user interfaces when neither the control center or robotic medical device system are in control of the robotic medical device in accordance with an embodiment. The graphical user interfaces 802, 804 shown are for control of an exemplary catheter procedure system (e.g., catheter procedure system 100 shown in FIGS. 2 and 3). When the control token is "free," the robotic medical device system is without the control token and the robotic medical device system may take control by taking the control token by, for example, actuating an "Enable All" button in the graphical user interface 802 for the robotic medical device system. The control center is also without the control token and can take control by, for example, actuating a "RCL Disabled" button for the robotic medical device system in the graphical user interface 804 for the control center. In an embodiment, the "Enable All" button of graphical user interface 804 may be shown with a background or color that indicates that the control center does not have control, for example, the text and background of the button may be greyed out.

Figure 12:
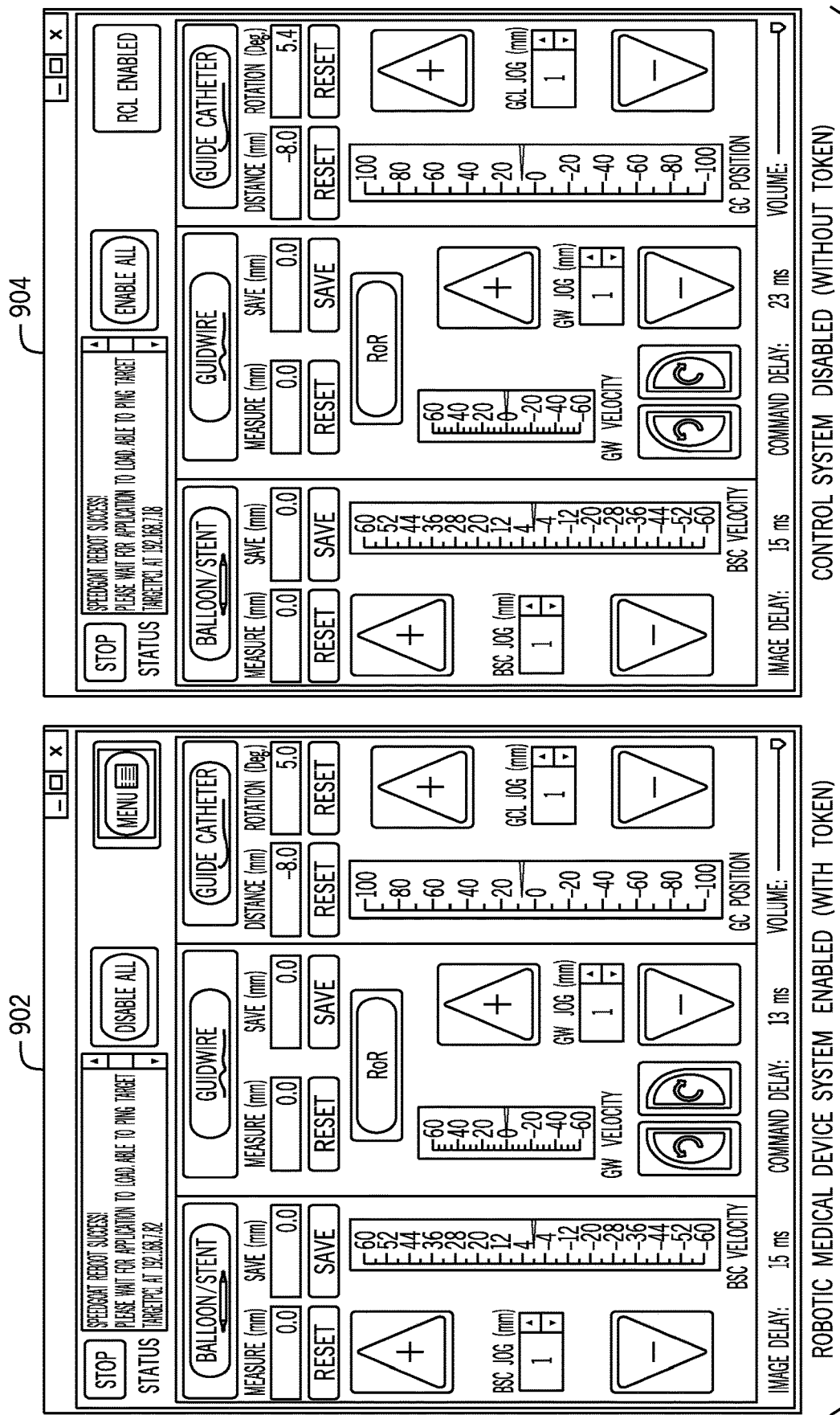
FIG. 12 shows exemplary user interfaces when the robotic medical device system is in control of the robotic medical device in accordance with an embodiment.

In a second state, the control token has been taken by the robotic medical device system 204. FIG. 12 shows exemplary user interfaces when the robotic medical device system is in control of the robotic medical device in accordance with an embodiment. The graphical user interfaces 902, 904 shown are for control of an exemplary catheter procedure system (e.g., catheter procedure system 100 shown in FIGS. 2 and 3). When the control token has been taken by the robotic medical device system, the robotic medical device system is given control and may be used to operate the robotic medical device. In FIG. 12, when the robotic medical device system has taken control with the control token, the "Enable All" button is disabled and changed to "Disable All" in graphical user interface 902 for the robotic medical device system. An operator may pass the control token back to being "free" by actuating the "Disable All" button. In the graphical user interface 904 for the control center, the "Disabled" button for the robotic medical device system is disabled. In an embodiment, the "Enable All" button and the "RCL Enabled button in the graphical user interface 904 may be shown with a background or color that indicates that the control center does not have control, for example, the text and background of the button may be greyed out.

Figure 13:
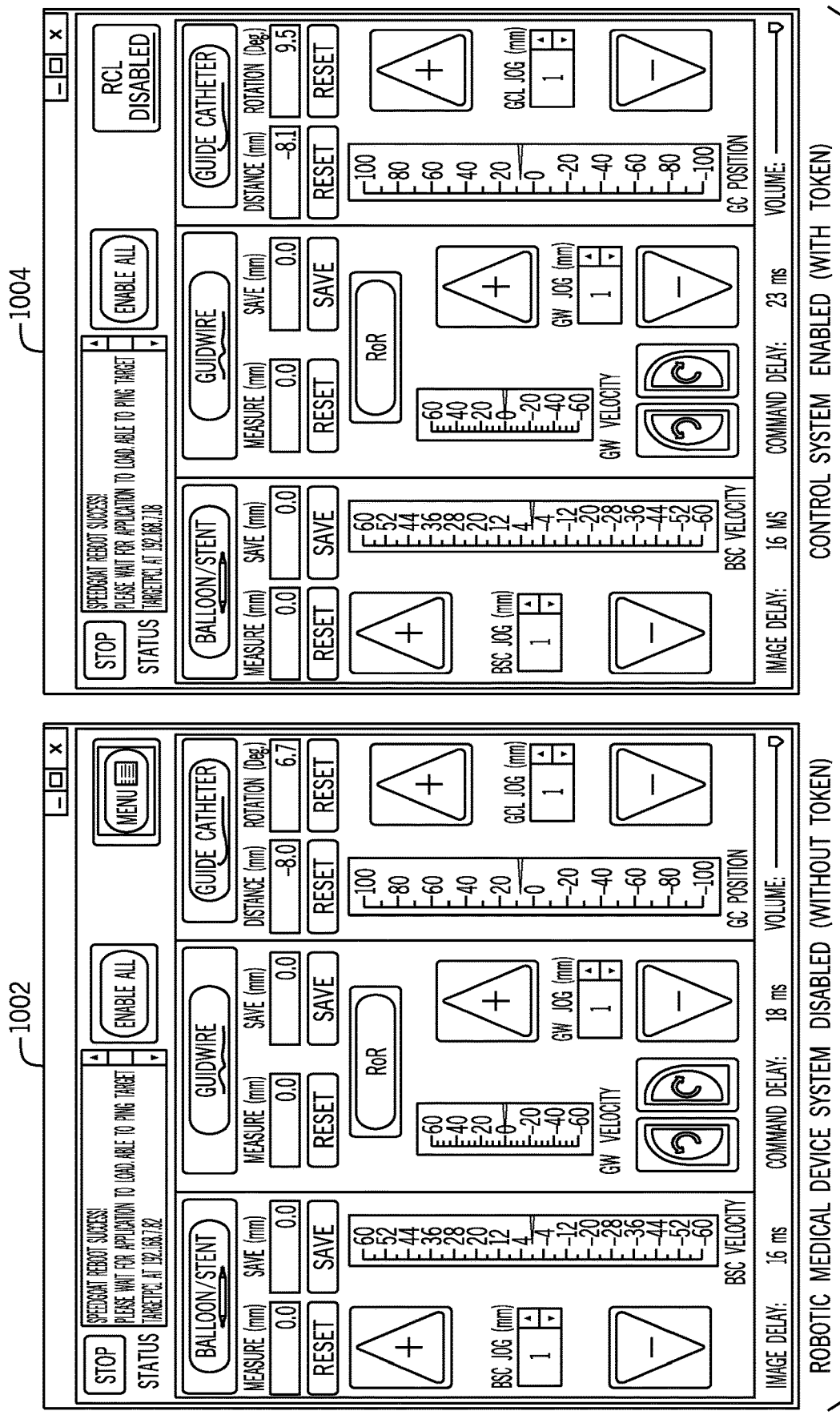
FIG. 13 shows exemplary user interfaces when the control center is in control of the robotic medical device in accordance with an embodiment.

In a third state, the control token has been taken by the control center 202. FIG. 13 shows exemplary user interfaces when the control center is in control of the robotic medical device in accordance with an embodiment. The graphical user interfaces 1002, 1004 shown are for control of an exemplary catheter procedure system (e.g., catheter procedure system 100 shown in FIGS. 2 and 3). When the control token has been taken by the control center, the control center is given control and may be used to operate the robotic medical device. In FIG. 13, when the control center has taken control with the control token, the "Enable All" button is enabled in graphical user interface 1004 for the control center. In addition, "RCL Disabled" in graphical user interface 1004 for the control center is enabled. In an embodiment, the "RCL Disabled" button of graphical user interface 1004 may be shown with a highlight, background or color that indicates that the control center has control. For example, graphical user interface 1004 is shown with an underline under "RCL Disabled." In another embodiment, the "RCL Disabled" button is shown in a color such as green. In the graphical user interface 1002 for the robotic medical device system, the "Enable All" button is disabled and the robotic medical device system is unable to take the control token. In an embodiment, the "Enable All" button of graphical user interface 1002 may be shown with a background or color that indicates that the robotic medical device system does not have control, for example, the text and background of the button may be greyed out.

In an embodiment, in the second and third state when one of the control center or the robotic medical device system has the control token, the site without the control token may have a request token or a force request token. The request token or force request token are virtual tokens implemented in software. The request token and force request token may be used to request control or to force a change in control. For example, if the control center has the control token the robotic medical device system may send a request token to the control center to request the control token be made "free" and available for the robotic medical device system to take the control token. In response to receiving the request token, the control center may, for example, make the control token "free", choose to keep the control token or timeout and keep the control token. In another example, if the control center has the control token the robotic medical device system may send a force request token to the control center to request the control token be made "free" and available for the robotic medical device system to take the control token. In response to the force request token, the control center may, for example, make the control token "free", choose to keep the control token or timeout and loose the control token.

Figure 16:
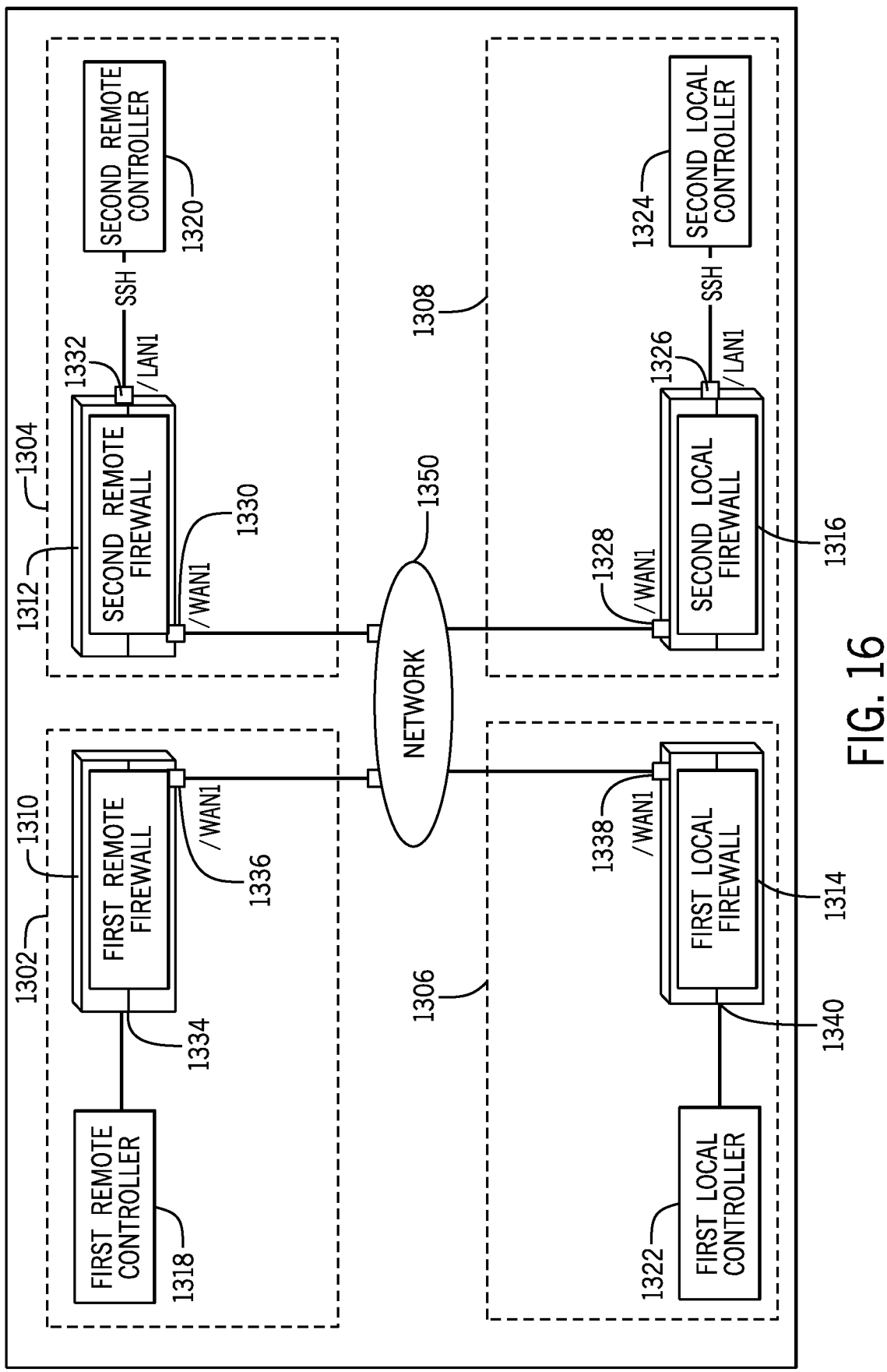
FIG. 16 is a block diagram of a many-to-many configuration of multiple control centers and multiple robotic medical device systems in accordance with an embodiment.

As discussed above with respect to FIGS. 3 and 4, multiple control centers 202 may be in communication with multiple robotic medical device systems 204 via a network 206 (e.g., a many-to-many configuration). FIG. 16 is a block diagram of a many-to-many configuration of multiple control centers and multiple robotic medical device systems in accordance with an embodiment. In FIG. 16, a first control center 1302, a second control center 1304, a first robotic medical device system 1306 and a second robotic medical device system 1308 are in communication over a network 1350. In an embodiment, each site (i.e., first control center 1302, second control center 1304, first robotic medical device system 1306 and second robotic medical device system 1308) may be at a different locations and may be remote from one another. The first control center 1302 is at a first remote site, the second control center 1304 is at a second remote site, the first robotic medical device system 1306 is at a first local site and the second robotic medical device system 1308 is at a second local site. The first control center 1302 may be used to control either the first robotic medical device system 1306 or the second robotic medical device system 1308. The second control center 1304 may be used to control either the first robotic medical device system 1306 or the second robotic medical device system 1308. The first control center 1302 includes a first remote firewall 1310, the second control center 1304 includes a second remote firewall 1312, the first robotic medical device system 1306 includes a first local firewall 1314 and the second robotic medical device system 1308 includes a second local firewall 1316. First remote firewall 1310 is coupled to a first remote controller 1318, second remote firewall 1312 is coupled to a second remote controller 1320, first local firewall 1314 is coupled to a first local controller 1322 and the second local firewall 1316 is coupled to a second local controller 1324. First remote firewall 1310 includes a LAN port 1334 and a WAN port 1336. Second remote firewall 1312 includes a LAN port 1332 and a WAN port 1330. First local firewall 1314 includes a LAN port 1340 and a WAN port 1338. Second local firewall 1316 includes a LAN port 1326 and a WAN port 1328.

Firewalls 1310, 1312, 1314 and 1316 are configured to establish a secure connection with another site and to take down the secure connection with another site. Preferably, control and management of establishing secure connections and taking down secure connections is handled automatically by each firewall and kept separate from the other hardware and software functions at each site. In one embodiment, a command line interface (CLI) and secure shell (SSH) protocol are used to establish a secure connection between two sites. In this embodiment, each firewall 1310, 1312, 1314 and 1316 has a unique static IP address. The following discussion will describe establishing a secure connection between the second control center 1304 and the second robotic medical device system 1308, however, the methods described herein may be used to establish and take down connections between any combination of sites in the many-to-many configuration. In one embodiment, a centralized approach is used. In the centralized approach, the WAN port 1330 of the second control center 1304 and the WAN port 1328 of the second robotic medical device system 1308 are open for SSH login. In this configuration, either site (e.g., second control center 1304 and second robotic medical device system 1308) may create a tunnel via its local firewall's LAN port and the WAN port of the other site. For example, the second local controller 1324 of the second robotic medical device system 1308 can SSH into the local LAN port 1326 of the second local firewall 1316 and the second local controller 1324 can SSH into the WAN port 1330 of the second remote firewall 1312 of the second control center 1304 to establish a tunnel. In another centralized approach example, the second remote controller 1320 of the second control center 1304 can SSH into the WAN port 1328 of the second local firewall 1316 of the second robotic medical device system 1308 and the second remote controller 1320 of the second control center 1304 can SSH the local LAN port 1332 of the second remote firewall 1312. In another embodiment, a decentralized approach is used. In the decentralized approach, the WAN port 1330 of the second control center 1304 and the WAN port 1328 of the second robotic medical device system 1308 do not allow for SSH login. In this embodiment, each site brings up its corresponding tunnel connection via its respective local firewall's LAN port such that the WAN ports can remain closed to SSH login for enhanced security. For example, the second local controller 1324 can SSH into LAN port 1326 and the second remote controller 1320 can SSH into the LAN port 1332.

In another embodiment, a secure connection may be established using patch panel direct routing where physically direct wiring is used between all of the sites (or nodes) on the patch panel. The connected ports may be switched when need to connect to a specific site. In yet another embodiment, a secure connection may be established by using two static IP addresses for all sites (or nodes). The same two static IP addresses are reserved on a routers for all of the sites. A site is only plugged in to the system (by a user) when it is being used and unplugged (by a user) from an Ethernet port when it is not being used. In another embodiment, a secure connection may be established using the same static IP address for all sites (or nodes). The static IP address and the Ethernet port mapping may be manually reconfigured on a router.

In another embodiment, the secure tunnel established between two firewalls is a secure virtual private network such as, for example, an IPSec tunnel. To establish an IPSec tunnel, in one example, the first control center 1302 and the first robotic medical device system 1306 have a shared key. The first local firewall 1314 of the first robotic medical device system 1306 brings up a tunnel pointing to the first remote firewall 1310 of the first control center 1302. The first remote firewall 1310 then brings up a tunnel pointing to the first local firewall 1314. In this example, neither site opens up their wan port to accept an SSH login. In another example, to establish an IPSec tunnel, the first local firewall 1314 allows for SSH logon. The first remote firewall 1310 logs on to the first local firewall 1314 using SSH. The first remote firewall 1310 then brings up the first local firewall's 1314 end of the tunnel to point to the first remote firewall 1310. The first remote firewall 1310 points its tunnel to the first local firewall 1314. The first remote firewall 1310 can then determine a key for both sites. In an embodiment, there is an a priori network topology map such that all local and remote sites are aware of their network locations.

In another embodiment, management of the multiple systems and connections in the many-to-many configuration may be managed using cloud computing. For example, a cloud-based infrastructure management solution may be used to manage the firewall at each site (or node). Each firewall (e.g., first remote firewall 1310, second remote firewall 1312, first local firewall 1314 and second local firewall 1316 shown in FIG. 16) are connected to the Internet and the cloud used for management. Cloud-based management allows an operator at one of the sites or at a separate location from the various sites to monitor and manage the firewalls.

Computer-executable instructions for a communications and control system according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A method for using a control center at a remote site to control operation of a robotic medical device system at a local site, the robotic medical device system including at least one medical device, and wherein the method comprises:
    transmitting a control signal from the control center to the robotic medical device system;
    determining a delay based on transmission of the control signal and transmission of an image from the robotic medical device system to the control center;
    comparing the delay to a threshold delay value; and
    operating the at least one medical device based on the comparison of the delay to the threshold delay value.

2. The method according to claim 1, wherein the operating the at least one medical device includes stopping a movement of the at least one medical device.

3. The method according to claim 1, wherein the operating the at least one medical device includes pausing a movement of the at least one medical device.

4. The method according to claim 1, wherein the operating the at least one medical device includes shifting control of the at least one medical device from the remote site to the local site.

5. A method for using a control center at a remote site to control operation of a robotic medical device system at a local site, the method comprising:
    transmitting a control signal from the control center to the robotic medical device system;
    determining a first delay in transmission of the control signal;
    transmitting at least one image from the robotic medical device system to the control center;
    determining a second delay in transmission of the at least one image;
    determining a total delay based on the first delay and the second delay; comparing the total delay to a threshold delay value; and
    operating the robotic medical device system based on the comparison of the total delay to the threshold delay value.

6. The method according to claim 1, further comprising: displaying the delay of the control signal on a display.

7. The method according to claim 5, further comprising: displaying the total delay on a display.

8. A method for using a control center at a remote site to control operation of a robotic medical device system at a local site, the method comprising:
    transmitting a control signal from the control center to the robotic medical device system;
    determining a first delay in transmission of the control signal;
    comparing the first delay to a threshold delay value;
    operating the robotic medical device system based on the comparison of the first delay to the threshold delay value;
    transmitting at least one image from the robotic medical device system to the control center;
    determining a second delay in transmission of the at least one image; and
    displaying the second delay on a display.

9. A method for using a control center at a remote site to control operation of an elongated medical device in a robotic medical device system at a local site, the method comprising:

receiving a control signal from the control center;
determining a delay in transmission of the control signal and transmission of an image from the robotic medical device system to the control center;
determining a threshold delay value based on at least one parameter of the robotic medical device system;
comparing the delay to the threshold delay value; and
adjusting the operation of the elongated medical device based on the comparison of the delay to the threshold delay value.

10. The method according to claim 9, wherein the at least one parameter of the robotic medical device system includes a type of procedure.

11. The method according to claim 9, wherein the at least one parameter of the robotic medical device system includes a type of elongated medical device.

12. The method according to claim 9, wherein the at least one parameter of the robotic medical device system includes a location of a tip of the elongated medical device.

13. The method according to claim 9, wherein the at least one parameter of the robotic medical device system includes a direction of movement of the elongated medical device.

14. The method according to claim 9, wherein the adjusting the operation of the elongated medical device includes stopping the elongated medical device in response to the delay being greater than the threshold delay value.

15. The method according to claim 9, wherein the adjusting the operation of the elongated medical device includes changing control of the elongated medical device to the robotic medical device system in response to the delay being greater than the threshold delay value.

16. The method according to claim 9, wherein the adjusting the operation of the elongated medical device includes adjusting a velocity of the elongated medical device.

17. The method according to claim 16, wherein the adjusting the velocity of the elongated medical device includes adjusting a velocity of advancement, retraction or rotation of the elongated medical device.

18. A method for using a control center at a remote site to control operation of a robotic medical device system at a local site, the method comprising:
receiving a control signal from the control center;
determining a delay based on transmission of the control signal and transmission of an image from the robotic medical device system to the control center;
comparing the delay to a threshold delay value;
adjusting a velocity of a medical device of the robotic medical device system when the delay is less than the threshold delay value, the velocity of the medical device being adjusted based on the delay; and
setting the velocity of the medical device to zero when the delay is greater than the threshold delay value.

19. The method according to claim 18, wherein the adjusting the velocity of the medical device of the robotic medical device system comprises decreasing the velocity of the medical device as the delay increases towards the threshold delay value.

20. The method according to claim 19, wherein the velocity of the medical device is given by:

$$v\_device = v\_command \times \max(t\_predetermined - t\_imagedelay, 0) / t\_predetermined.$$

21. The method according to claim 18, wherein the delay is a total network delay obtained based on a delay in the transmission of the control signal and a delay in the transmission of the image from the robotic medical device system to the control center.

22. The method according to claim 21, wherein the velocity of the medical device is given by:

$$v\_device = v\_command \times \max(t\_predetermined - t\_imagedelay, 0) / t\_predetermined.$$

23. The method according to claim 18, wherein the medical device is an elongated medical device and the robotic medical device system is a catheter procedure system.

24. A system for controlling at least one medical device, the system comprising:
a control center located at a remote site, the control center including
a control console,
a first command and control module coupled to the control console, and
a first clock coupled to the first command and control module and using a precision time protocol, the first clock configured to receive first time data from a reference time source; and
a robotic medical device system at a local site, the robotic medical device system in communication with the control center, and the robotic medical device system including
the at least one medical device,
a second command and control module coupled to the at least one medical device and in communication with the first command and control module, and
a second clock coupled to the second command and control module and using the precision time protocol, the second clock configured to receive second time data from the reference time source;
wherein the control center and the robotic medical device system communicate over a secure tunnel;
wherein the control console of the control center is configured to communicate with and control the at least one medical device;
wherein the first command and control module is configured to transmit a control signal from the control center to the robotic medical device system, the control signal including a timestamp generated based on the first time data; and
wherein the second command and control module is configured to operate the at least one medical device based on the timestamp.

25. The system according to claim 24, further comprising:
a plurality of control centers and a plurality of robotic medical device systems, wherein each of the plurality of robotic medical device systems is in communication with each of the plurality of control centers.

26. The system according to claim 24, wherein
the control center includes a first firewall coupled to the first command and control module,
the robotic medical device system includes a second firewall coupled to the second command and control module, and
the first firewall is configured to establish a secure tunnel with the second firewall.

27. The system according to claim 26, wherein the secure tunnel is an IPsec tunnel.

28. The system according to claim 24, wherein the reference time source is a satellite-based time source.

29. The system according to claim 28, wherein the satellite-based time source is a global positioning system.

30. The system according to claim 28, wherein the satellite-based time source is a satellite time and location system.

31. A system for managing control of at least one medical device by a remote site and a local site, the system comprising:
- a control center located at the remote site;
- a robotic medical device system at the local site, the robotic medical device system including the at least one medical device and being in communication with the control center;
- a virtual control token for determining a control state for the control center and the robotic medical device system, wherein a location of the virtual control token determines the control state;
- wherein the control center or the robotic medical device system is in control of the at least one medical device based on the control state; and
- wherein, in a free state, the virtual control token is free and available to be taken by the control center or the robotic medical device system to obtain control of the at least one medical device.

32. The system according to claim 31, wherein, in a first control state, the virtual control token is located at the control center and the control center is in control of the at least one medical device.

33. The system according to claim 31, wherein in a second control state, the virtual control token is located at the robotic medical device system and the robotic medical device system is in control of the at least one medical device.

34. The system according to claim 31, further comprising:
- a virtual request token for requesting control of the at least one medical device.

35. The system according to claim 31, further comprising:
- a virtual force request token for taking control of the at least one medical device.

36. A method for reducing bandwidth for transmission of data from a robotic medical device system at a local site to a control center at a remote site, in a system for performing a remote medical procedure, the control center configured to control operation of the robotic medical device system, and the method comprising:
- generating a display of the data at the robotic medical device system, wherein the data includes at least one image and non-image patient information, the at least one image including an image of a region of interest of a patient;
- selecting a section of the generated display;
- transmitting the selected section of the generated display to the control center; and
- displaying the selected section on a display at the control center.

* * * * *